United States Patent [19]

Mulligan et al.

[11] Patent Number: 5,521,076
[45] Date of Patent: May 28, 1996

[54] MODIFIED HEPATOCYTES AND USES THEREFOR

[75] Inventors: Richard C. Mulligan, Lincoln, Mass.; James M. Wilson, Ann Arbor, Mich.

[73] Assignees: Whitehead Institute For Biomedical Research, Cambridge, Mass.; Howard Hughes Medical Center, Bethesda, Md.

[21] Appl. No.: 938,260

[22] PCT Filed: Dec. 23, 1991

[86] PCT No.: PCT/US91/09700

§ 371 Date: Oct. 22, 1992

§ 102(e) Date: Oct. 22, 1992

[87] PCT Pub. No.: WO92/12242

PCT Pub. Date: Jul. 23, 1992

Related U.S. Application Data

[63] Continuation-in-part of Ser. No. 152,749, Feb. 5, 1988, abandoned.

[51] Int. Cl.$^6$ .............................. C12N 15/00; C12N 5/00
[52] U.S. Cl. .................................. 435/172.3; 435/240.2; 435/69.1; 435/320.1; 435/948; 424/93.21; 424/93.2; 935/70; 935/71; 935/62; 935/57; 935/11; 935/13; 935/32; 935/107
[58] Field of Search .......................... 435/172.3, 240.2, 435/69.1, 320.1, 948; 935/70, 71, 62, 107, 57, 11, 13, 32; 424/93 B, 93.21, 93.2

[56] References Cited

U.S. PATENT DOCUMENTS

| 4,497,796 | 2/1985 | Salser et al. | 424/95 |
|---|---|---|---|
| 4,686,098 | 8/1987 | Kopchick et al. | 424/424 |
| 4,868,116 | 9/1989 | Morgan et al. | 435/240.2 |
| 4,980,286 | 12/1990 | Morgan et al. | 435/172.3 |
| 5,399,346 | 3/1995 | Anderson et al. | 424/93.21 |

FOREIGN PATENT DOCUMENTS

WO89/07136  8/1989  WIPO .
WO90/06757  6/1990  WIPO .

OTHER PUBLICATIONS

Leffert et al., In "Methods for serum-free culture of epithelial and fibroblastic cells," eds Barnes et al., Alan Liss Inc., pp. 43–55 (1984).

Ledley et al., Proc. Natl. Acad. Sci. 83: 409–413 (1986).
Miller et al., In "Cold Spring Harbor Symp. Quant. Biol.", vol. LI, pp. 1013–1019 (1986), Cold Spring Harbor Lab.
Verma et al., Current Opinion in Genetics & Devel. 1: 54–59 (1991).
Ledley, et al., "Retroviral gene transfer into primary hepatocytes: Implications for genetic therapy of liver–specific functions", *Proc. Natl. Acad. Sci. USA* 84: 5335–5339 (1987).
Wolff, et al., "Expression of retrovirally transduced genes in primary cultures of adult rat hepatocytes", *Proc. Natl. Acad. Sci. USA* 84: 3344–3348 (1987).
Wilson, et al., "Correction of the genetic defect in hepatocytes from the Watanabe heritable hyperlipidemic rabbit", *Proc. Natl. Acad. Sci. USA* 85: 4421–4425 (1988).
Wilson, et al., "Retrovirus–mediated transduction of adult hepatocytes", *Proc. Natl. Acad. Sci. USA* 85: 3014–3018 (1988).
Peng, et al., "Retroviral–mediated gene transfer and expression of human phenylalanine hydroxylase in primary mouse hepatocytes", *Proc. Natl. Acad. Sci. USA* 85: 8146–8150 (1988).
Wilson, et al., "Temporary amelioration of hyperlipidemia in low density lipoprotein receptor–deficient rabbits transplanted with genetically modified hepatocytes", *Proc. Natl. Acad. Sci. USA* 87: 8437–8441 (1990).
Friedmann, et al., "Retrovirus Vector–mediated Gene Transfer into Hepatocytes", *Mol. Biol. Med.* 6: 117–125 (1989).
Morgan, et al., "Expression of an Exogenous Growth Hormone Gene by Transplantable Human Epidermal Cells" *Science* 237: 1476–1479 (1987).
Yamamoto, et al., "The Human LDL Receptor: A Cysteine–Rich Protein with Multiple Alu Sequences in Its mRNA", *Cell* 39: 27–38 (1984).
Demetriou, Achilles A. "Hepatocyte Transplantation". *Scientific American* (Nov./Dec. 1994) pp. 58–67.

*Primary Examiner*—Jasemine C. Chambers
*Attorney, Agent, or Firm*—Albert P. Halluin; Pennie & Edmonds

[57] ABSTRACT

Genetically engineered or transduced hepatocytes which express genetic material of interest introduced or incorporated into them, as well as methods of producing, transplanting and using the genetically engineered hepatocytes are disclosed. The genetic material of interest can be incorporated through the use of a vector, such as a recombinant retrovirus, which contains the genetic material of interest, or by other means.

5 Claims, 15 Drawing Sheets

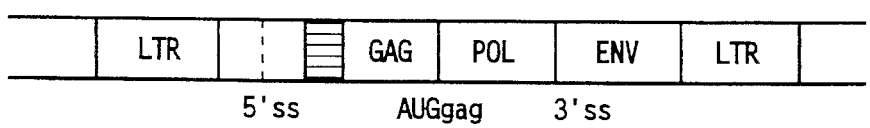
FIG. 1
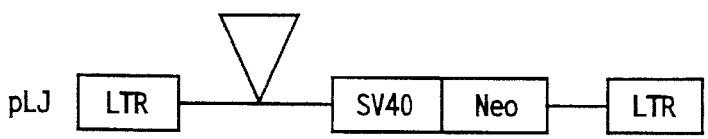
FIG. 2a
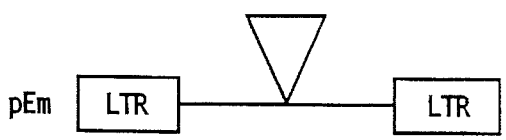
FIG. 2b
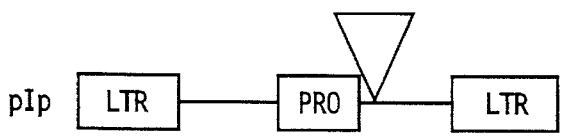
FIG. 2c
PRO = β-ACTIN
HISTONE
THYMIDINE KINOSE
THY-1
ALBUMIN
FIG. 3
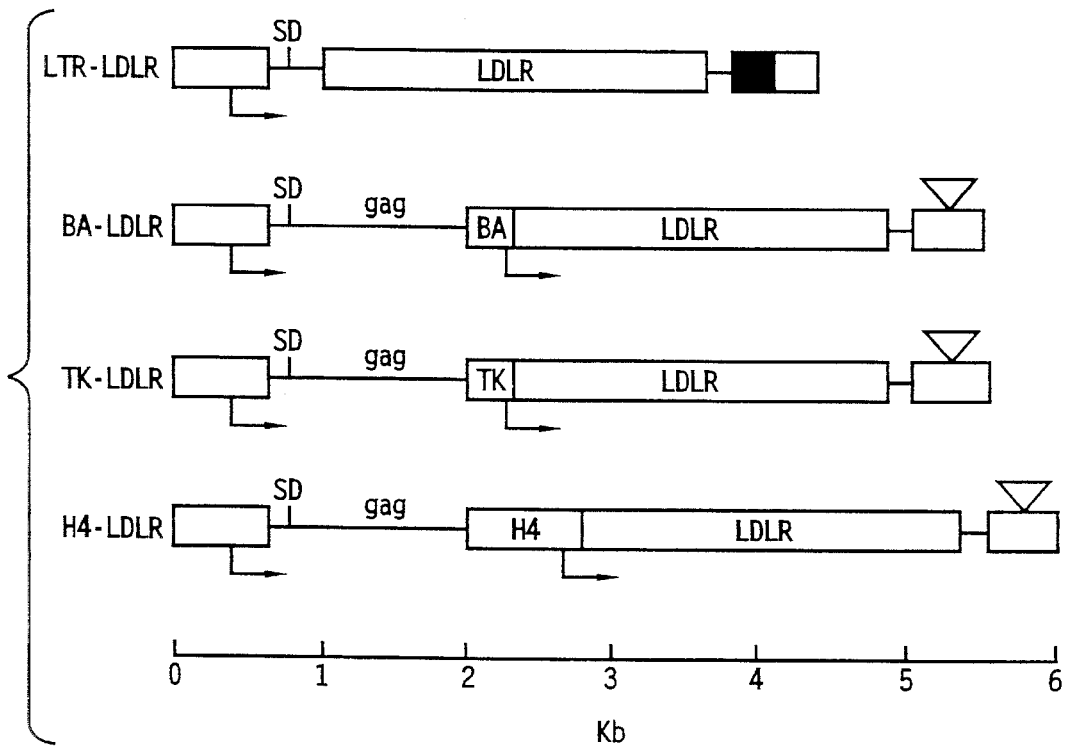

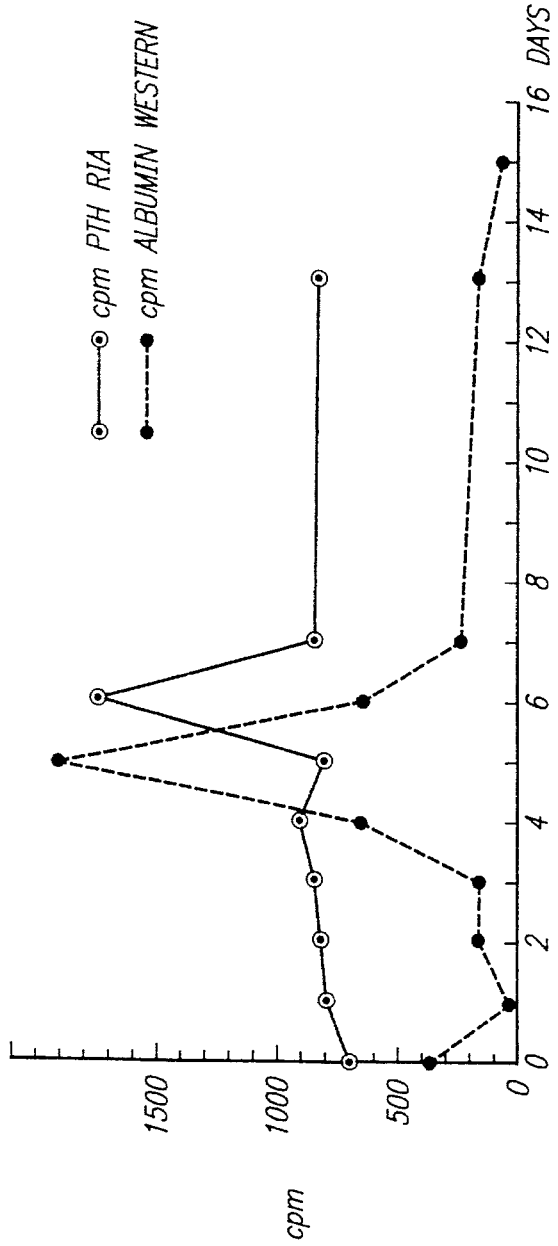
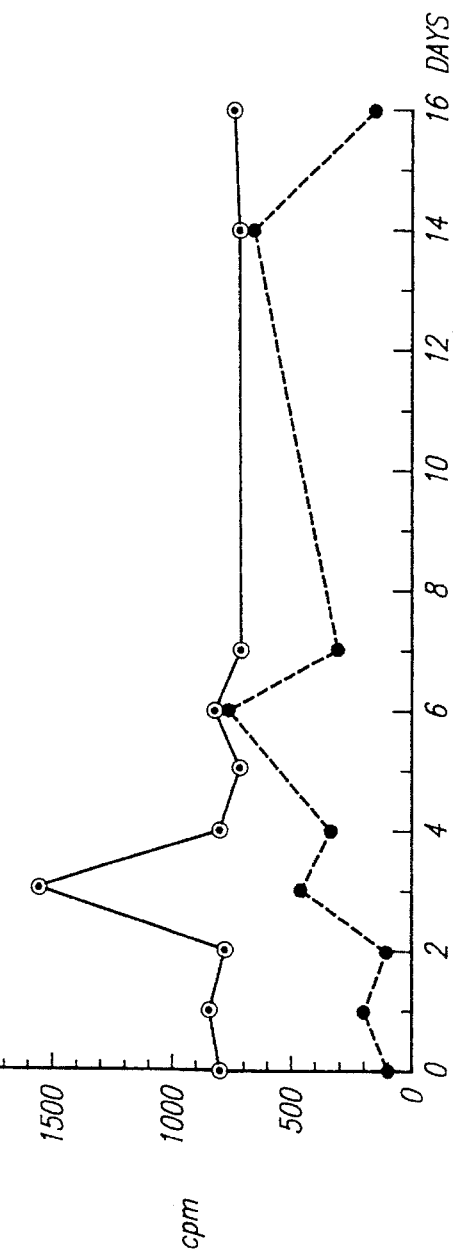
FIG. 8A
FIG. 8B

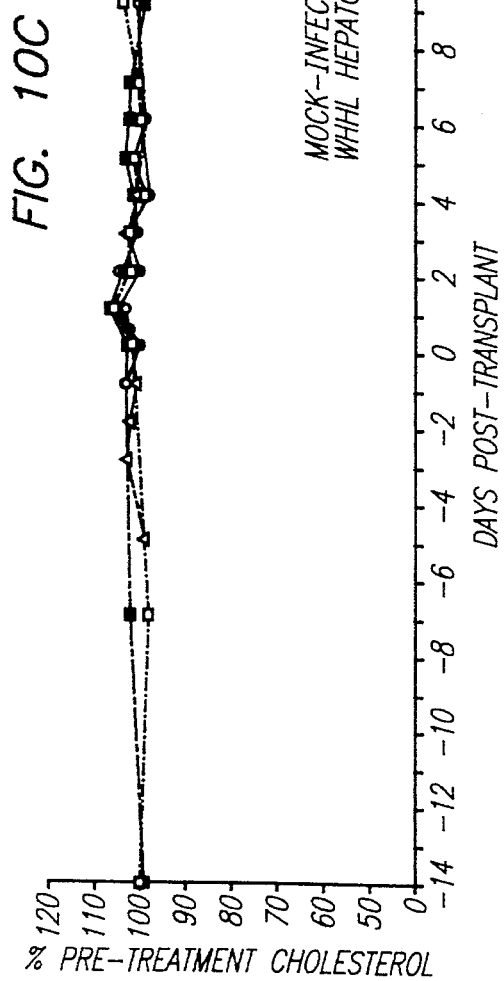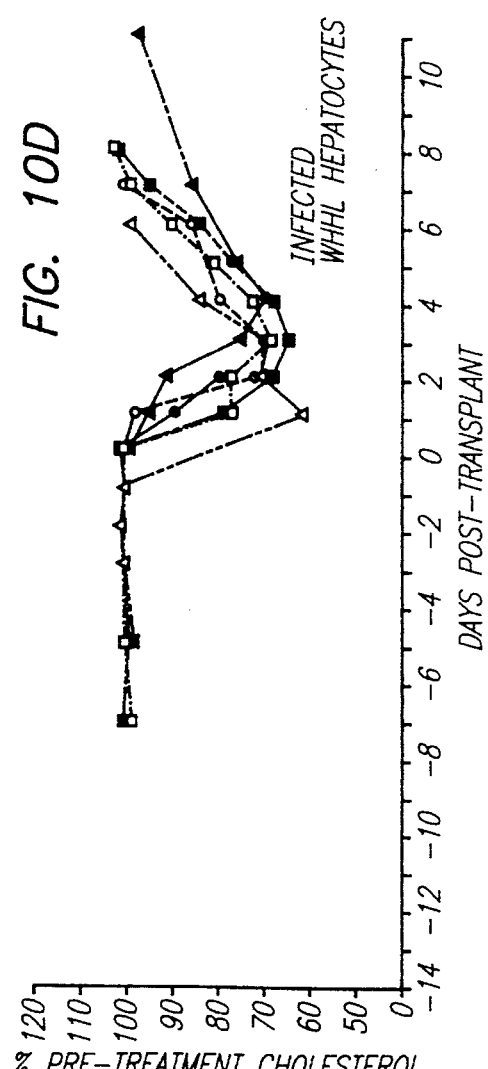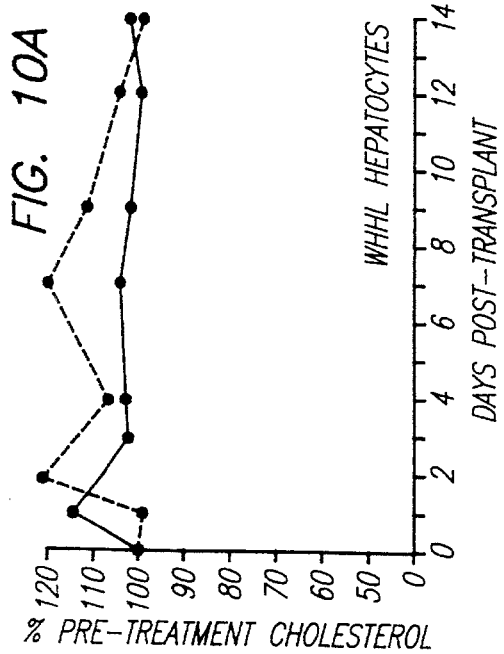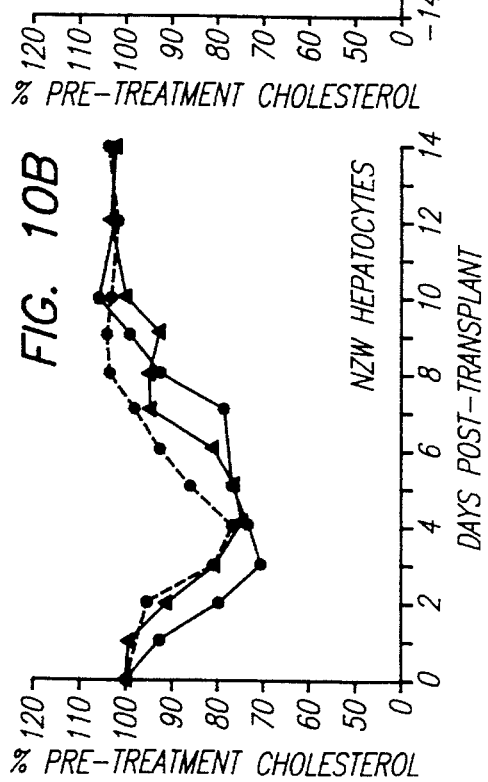

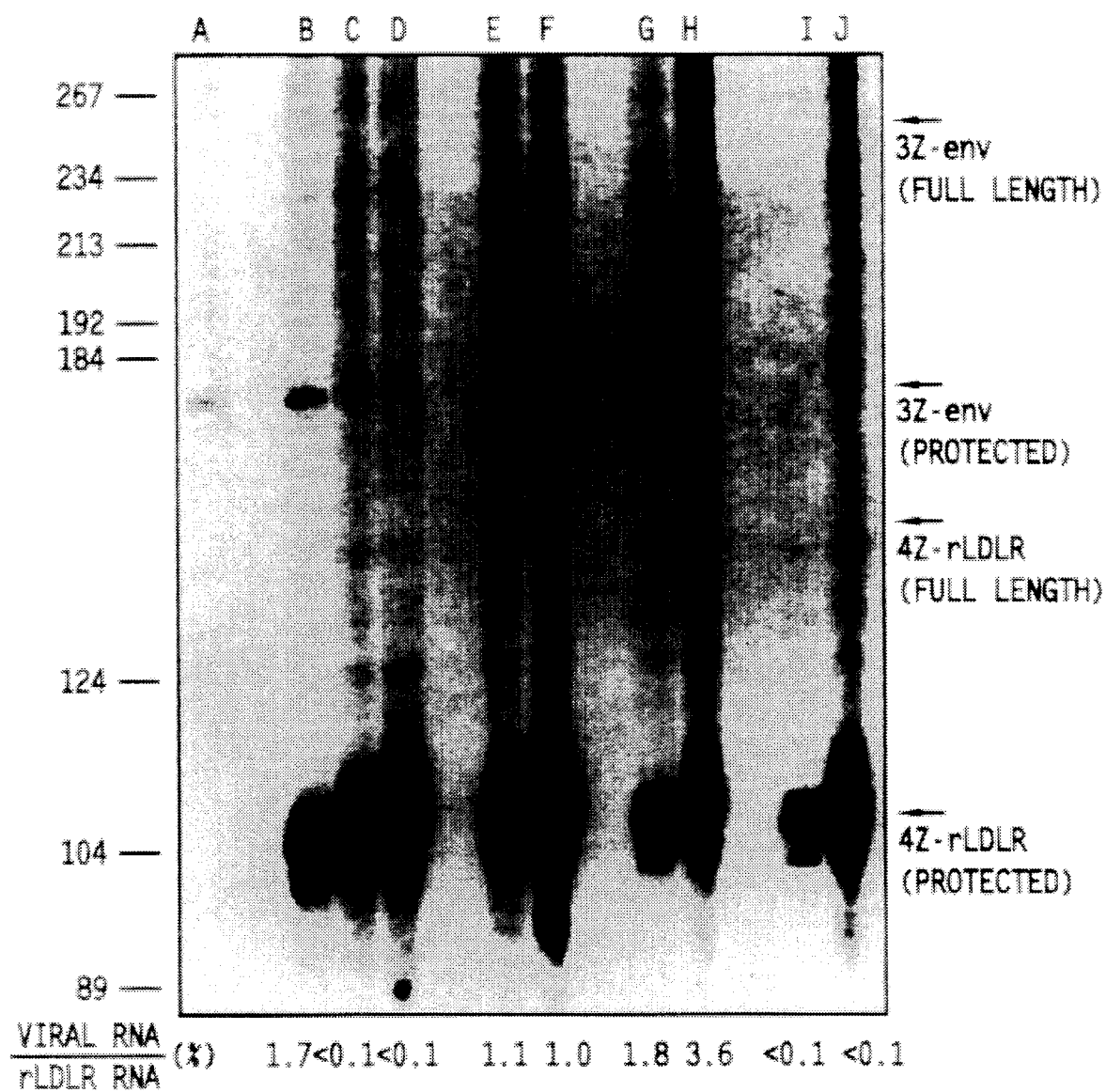

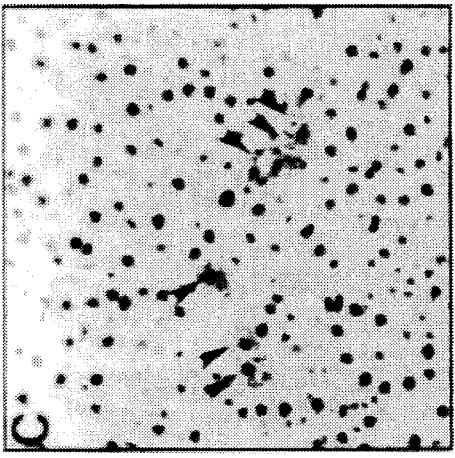
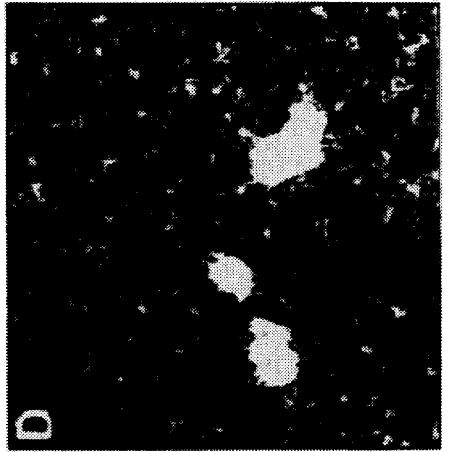
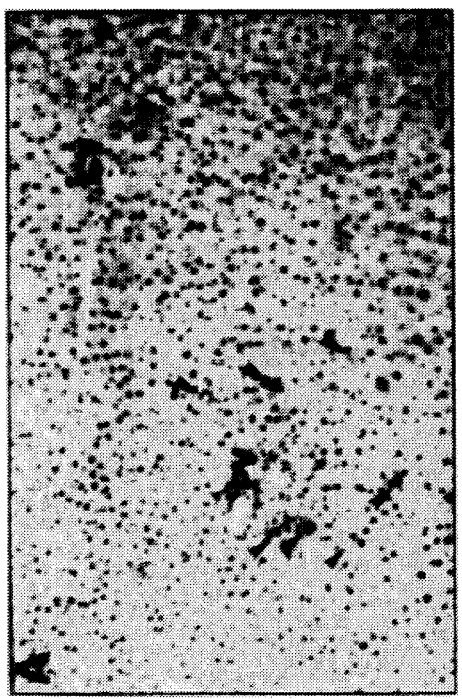
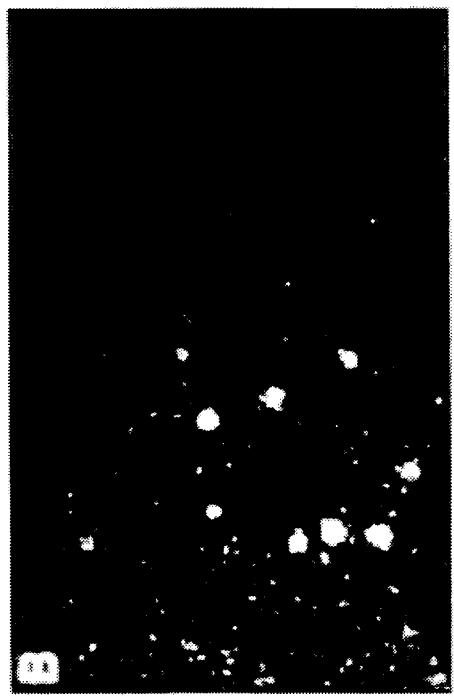

MODIFIED HEPATOCYTES AND USES THEREFOR

FUNDING

Work described herein was funded by the Howard Hughes Medical Institute, the National Institutes for Health and the Whitehead Institute for Biomedical Research.

RELATED APPLICATION

This is a continuation-in-part of U.S. application Ser. No. 07/152,749, filed Feb. 5, 1988, now abandoned.

BACKGROUND

The liver is of endodermal origin and the largest gland in the human body. It has numerous crucial roles, including bile secretion, participation in carbohydrate; lipid and protein metabolism, fibrinogen production and detoxification of drugs. The liver also serves as the main site at which nutrients absorbed from the gastro-intestinal tract and transported via the blood are processed for use by other body cells.

Hepatocytes, which are the main type of parenchymal or distinguishing cell in the liver, carry out the liver functions and, thus, are responsible for synthesizing, degrading and storing a wide variety of substances. In addition, a system of small channels (canaliculi) and larger ducts connects hepatocytes with the gut lumen. Through this route, hepatocytes secrete bile, an emulsifying agent which helps in absorption of ingested fats. Hepatocytes are also the main location at which lipoprotein particles for export are made; enzymes responsible for synthesis of the lipid constituents of lipoproteins occur in hepatocyte membranes.

Because of the many important functions the liver has, its inability to function normally (e.g., as a result of a genetic defect or damage caused by alcohol or other toxic substances) will often have significant adverse effects on an individual's health. A means by which normal function can be conferred upon or restored to a liver whose function is compromised would be very useful in treating, correcting or preventing such an abnormality.

SUMMARY OF THE INVENTION

The invention described herein relates to genetically engineered or transduced hepatocytes which express genetic material (DNA or RNA) of interest introduced or incorporated into them, as well as to methods of producing, transplanting and using the genetically engineered hepatocytes. The genetic material of interest can be incorporated through the use of a vector, such as a recombinant retrovirus, which contains the genetic material of interest, or by other means.

Hepatocytes of the present invention express the genetic material of interest. Such genetic material of interest can be: 1) genetic material present in and expressed at biologically effective levels by normal hepatocytes, but present in or expressed in less than normal quantities in the hepatocytes prior to transfer of genetic material of interest into them by the method of the present invention; 2) genetic material not present in normal hepatocytes; or 3) genetic material present in normal hepatocytes but not expressed at biologically effective levels in such cells, alone or in any combination thereof.

In hepatocytes of the present invention, the genetic material of interest can be incorporated into the celluar genetic material (e.g., into genomic DNA) Or can be present extrachromosomally (i.e., expressed episomally). The genetic material of interest can be DNA or RNA; the DNA can constitute all or a portion of a gene of interest (i.e., one whose expression in hepatocytes is desired).

The genetic material incorporated into and expressed by hepatocytes of the present invention can additionally include genetic material (e.g., DNA) encoding a selectable marker, which provides a means by which cells expressing the genetic material of interest are identified and selected for. Hepatocytes containing incorporated genetic material (i.e., genetic material of interest and, optionally, genetic material encoding a selectable marker) are referred to as transduced hepatocytes.

Genetic material can be introduced into hepatocytes ex vivo or in vivo. That is, it can be introduced, by means of an appropriate vector, into isolated (cultured) hepatocytes, which are subsequently transplanted into the recipient. Alternatively, it can be introduced directly into the recipient in such a manner that it is directed to and taken up by target cells (hepatocytes), where it is incorporated and expressed. Particularly useful for this purpose are retroviral vectors which have an amphotropic host range and include the genetic material of interest which is to be incorporated into hepatocytes.

Retroviral vectors have been used to stably transduce hepatocytes with genetic material which included genetic material encoding a polypeptide or protein of interest and genetic material encoding a dominant selectable marker. Genetic material including DNA encoding a polypeptide of interest and DNA encoding a dominant selectable marker has been introduced into cultured hepatocytes. Expression of the genetic material by the hepatocytes into which they have been incorporated has also been demonstrated.

A method of transplanting transduced hepatocytes which express the incorporated genetic material they contain is also a subject of the present invention. Transduced hepatocytes of the present invention are used, for example, for the delivery of polypeptides or proteins which are useful in prevention and therapy of an acquired or an inherited defect in hepatocyte (liver) function. For example, they can be used to correct an inherited deficiency of the low density lipoprotein receptor (LDLR), which is synthesized in hepatocytes, and to correct an inherited deficiency of ornithine transcarbalyase (OTC), which results in congenital hyperammonemia.

Hepatocytes of the present invention are useful as a means by which abnormal hepatocyte function can be corrected. That is, hepatocytes can be transduced with genetic material of interest selected to compensate for over- or underproduction of a protein or peptide which is synthesized correctly, but in inappropriate amounts in the hepatocytes. Alternatively, they can be transduced with genetic material of interest encoding a protein or polypeptide which is produced in an appropriate quantity, but is functionally defective (e.g., because of an abnormal structure or amino acid makeup).

Hepatocytes to be modified ex vivo, as described herein, can be obtained from an individual, modified and returned to the individual by transplanting or grafting or, alternatively, can be obtained from a donor (i.e., a source other than the ultimate recipient), modified and applied to a recipient, again by transplanting or grafting.

An important advantage of the procedure of the present invention is that the genetically engineered hepatocytes can be used to provide a desired therapeutic protein or peptide by a means essentially the same as that by which the protein or peptide is normally produced and, in the case of autologous grafting, with little risk of an immune response and graft rejection. In addition, there is no need for extensive (and often costly) purification of a polypeptide before it is administered to an individual, as is generally necessary with an isolated polypeptide. Hepatocytes modified according to the present invention produce the polypeptide as it would normally be produced.

Because genes can be introduced into hepatocytes using a retroviral vector, they can be on, (subject to) the retroviral vector control; in such a case, the gene of interest is transcribed from a retroviral promoter. A promoter is a specific nucleotide sequence recognized by RNA polymerase molecules that start RNA synthesis. Alternatively, retroviral vectors having additional promoter elements (in addition to the promoter incorporated in the recombinant retrovirus), which are responsible for the transcription of the genetic material of interest, can be used. For example, a construct in which there is an additional promoter modulated by an external factor or cue can be used, making it possible to control the level of polypeptide being produced by the modified hepatocytes by activating that external factor or cue. For example, heat shock proteins are proteins encoded by genes in which the promoter is regulated by temperature. The promoter of the gene which encodes the metal-containing protein metallothionine is responsive to cadmium ($Cd^{++}$) ions. Incorporation of this promoter or another promoter influenced by external cues also makes it possible to regulate the production of the polypeptide by the engineered hepatocytes.

BRIEF DESCRIPTION OF THE DRAWINGS

FIG. 1 is a schematic representation of a wild type murine leukemia virus (retroviral) genome.

FIGS. 2A–2C is a schematic representation of retroviral vectors, each having a recombinant genome, which are useful in the present invention. FIG. 2a is pLJ; FIG. 2b is pEm; and FIG. 2c is pIp.

FIG. 3 is a schematic representation of vectors which express human-LDLR. Each has a different transcriptional element which drives expression of LDLR: LTR-LDLR, viral long term repeat sequences (LTR); BA-LDLR, promoter from chicken beta-actin gene (BA); H4-LDLR, promoter from human histone H4 gene (H4); TK-LDLR, promoter from thymidine kinase gene of herpes simplex virus (TK).

FIG. 8 is a graphic representation of human parathyroid hormone (PTH) production by transduced rat hepatocytes and of rat albumin production by control hepatocytes.

Panel A: Retroviral vector. The strategy used to clone this vector is described in 'Methods'. Vector sequences involved in the production of appropriate probes are expanded in the area below the vector. The RNA probe complementary to viral sequences in the recombinant transcript is noted; a 172 bp transcript should be protected to digestion with RNase. The 5' and 3' PCR oligonucleotides are derived from human LDL receptor cDNA sequences, and flanking viral sequences, respectively, as shown; a 495 bp fragment is amplified with these oligonucleotides.

Panel B: Southern blot analysis. Total cellular DNA was isolated and analyzed (10 μg/lane) for proviral sequences as described in "Methods" DNA from mock-infected hepatocytes plus 1.25 pg of LTR-LDLR plasmid, lane "Plasmid"; DNA from mock-infected hepatocytes, lane "Mock"; DNA from hepatocytes infected with LTR-LDLR virus, lane 'Infected'.

Panel C: RNA blot analysis; was performed on total cellular RNA as described in "Methods". Samples were derived from HepG2 (5 μg), and hepatocytes infected with the LTR-LDLR virus (5, 1 and 0.2 μg). HepG2 cells were grown in medium containing lipoprotein deficient serum prior to harvest for RNA.

FIG. 10 shows the effect of hepatocyte transplantation on cholesterol metabolism in WHHL rabbits.

Donor hepatocytes were transplanted into WHHL rabbits as described in "Methods". Total serum cholesterol, presented as the % pretreatment level, was measured as a function of time following transplantation which occurred on Day 0. Data are plotted for each animal.

Panel A: WHHL hepatocytes were transplanted into two animals.

Panel B: NZW hepatocytes were transplanted into three animals.

Panel C: Mock-infected WHHL hepatocytes were transplanted into six WHHL recipients.

Panel D: LTR-LDLR infected WHHL hepatocytes were transplanted into seven recipients.

Figure 11:
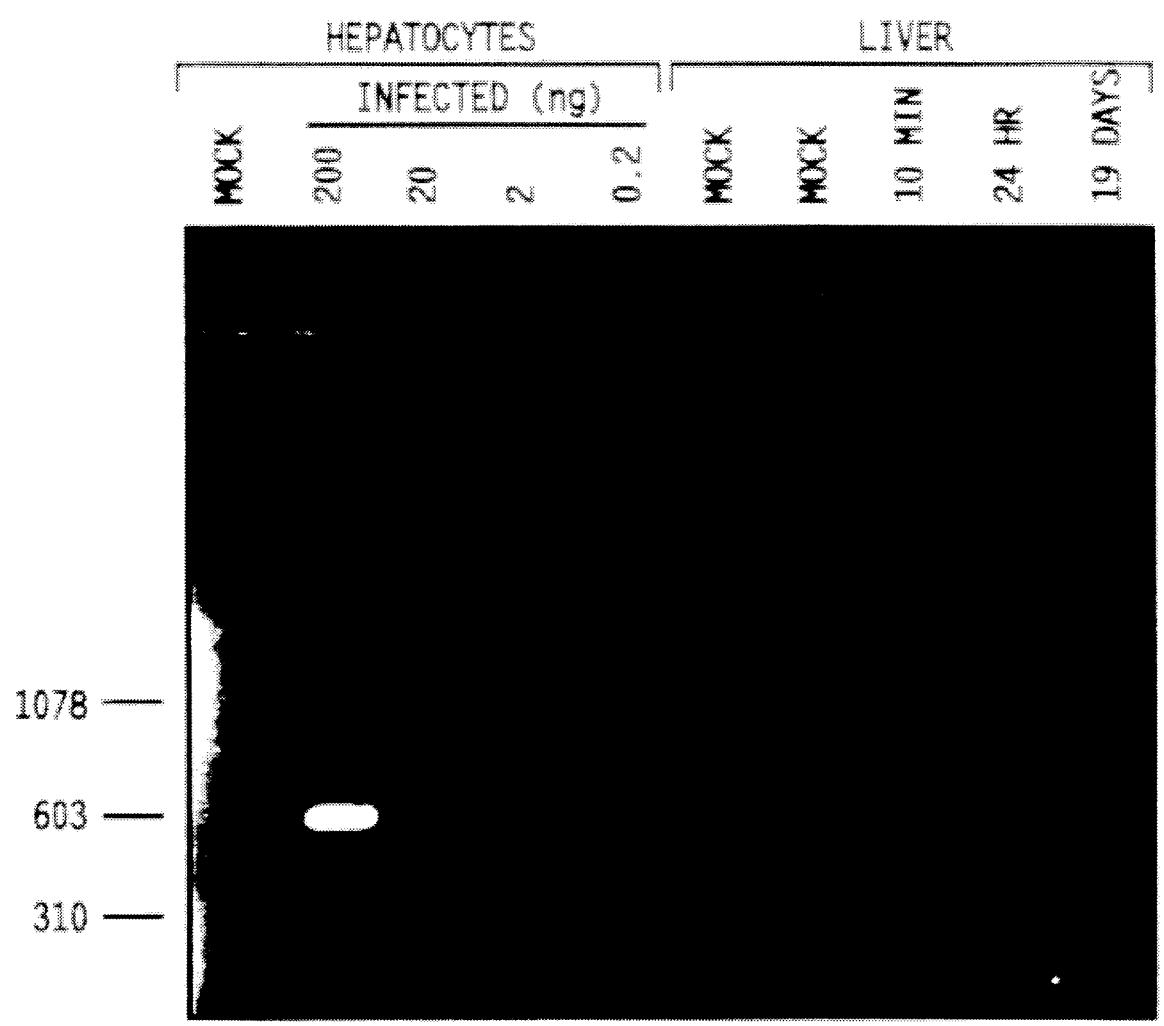

FIG. 11 shows results of analysis of liver tissue for proviral DNA sequences by PCR.

Total cellular DNA was isolated from hepatocytes and liver tissues and analyzed for proviral sequences using the polymerase chain reaction. Hepatocyte DNA was from mock-infected (200 ng) and LTR-LDLR infected hepatocytes (200, 20, 2 and 0.2 ng). Liver DNA from each tissue was isolated on separate occasions with identical results; representative assays are presented. Samples were from control WHHL rabbits (mock) and livers harvested from transplant recipients 10 minutes, 24 hours, and 19 days following the transplant.

FIG. 12 shows results of RNase protection assays.

Total cellular RNA samples were hybridized with two [32] labeled RNA probes (3Z-env and 4Z-rLDLR) and analyzed for protection to digestion with RNase A. These include:

Lane A: tRNA (100 μg) plus virus produced (100 ng);

Lane B: WHHL (100 ng) plus virus producer (100 ng);

Lane C: WHHL control (100 μg);

Lane D: WHHL control (250 μg);

Lane E: WHHL 10 minutes (100 μg);

Lane F: WHHL 10 minutes (250 μg);

Lane G: WHHL 24 hours (100 μg);

Lane H: WHHL 24 hours (250 μg);

Lane I: 19 days (100 μg); and

Lane J: 19 days (250 μg).

Molecular size standards measured in bp and noted along the left border. Locations of the full length and protected RNA probes, 3Z-env and 4Z-rLDLR, are noted on the right border. Radioactivity in individual bands were measured with a Betagen Scanner (Betagen Co.). The ratio of radioactivity in the virus specific band to that in the endogenous band is noted below each lane as %.

FIG. 13 shows results of in situ hybridization of liver from transplant recipients.

Cryostat sections of liver were hybridized with the virus specific RNA probe as described in 'Methods'. These tissues were derived from a WHHL rabbit 24 hours after transplantation with LTR-LDLR transduced hepatocytes. Slides were counter stained with hematoxylin.

Panels A and B: Bright field (A) and dark field (B) views of an area demonstrating periportal distribution of transplanted cells. P.V. indicates portal vessels and a probable biliary ductule. Cells which are clearly positive in the dark field are indicated by arrows in the bright field (magnification—70 ×).

Panels C and D: Higher power magnification (×250) of transplanted hepatocytes visualized on a bright field (C) and a dark field (D).

Figure 14:
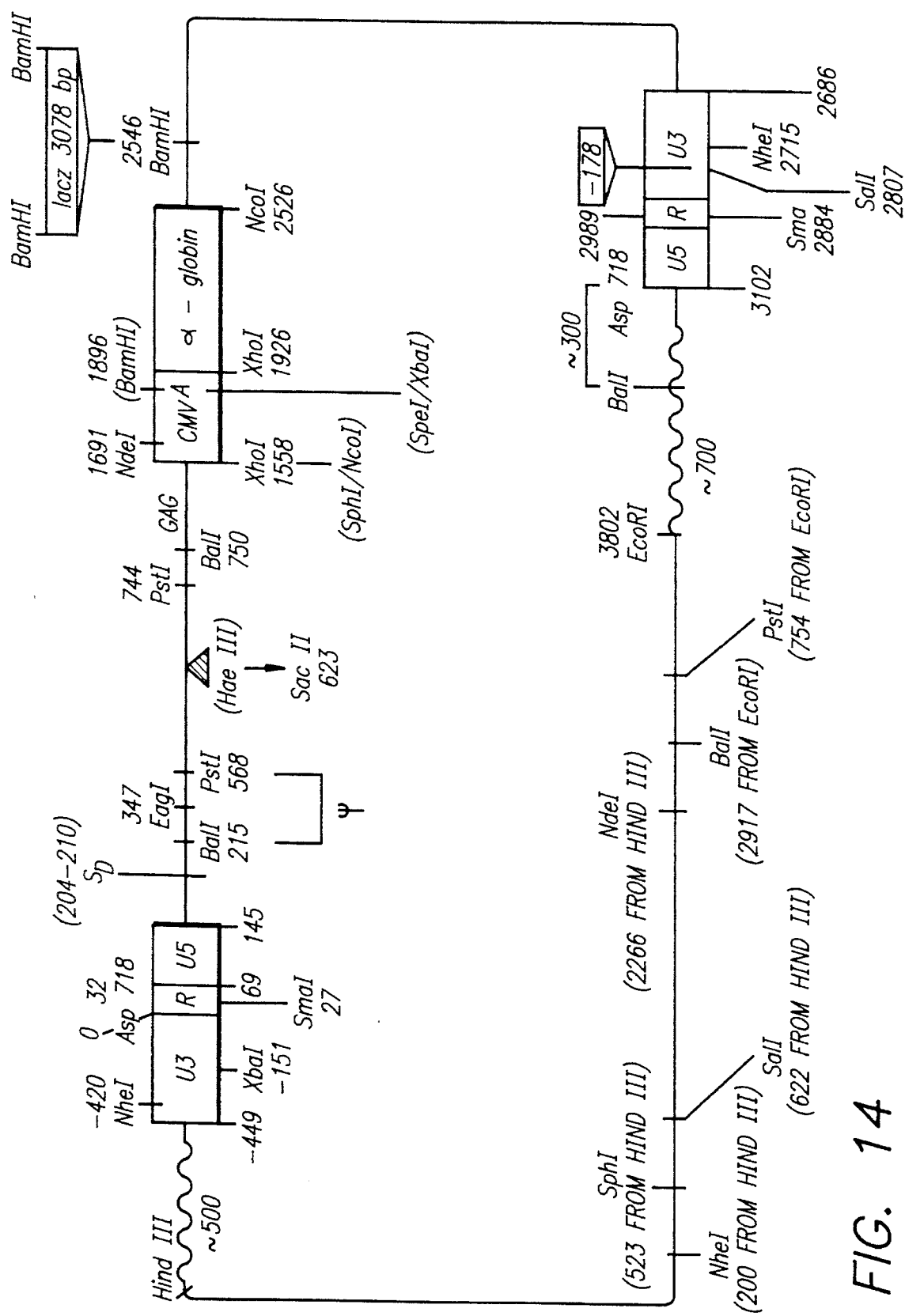

FIG. 14 is a schematic diagram of the retroviral vector MFG.

Figure 15:
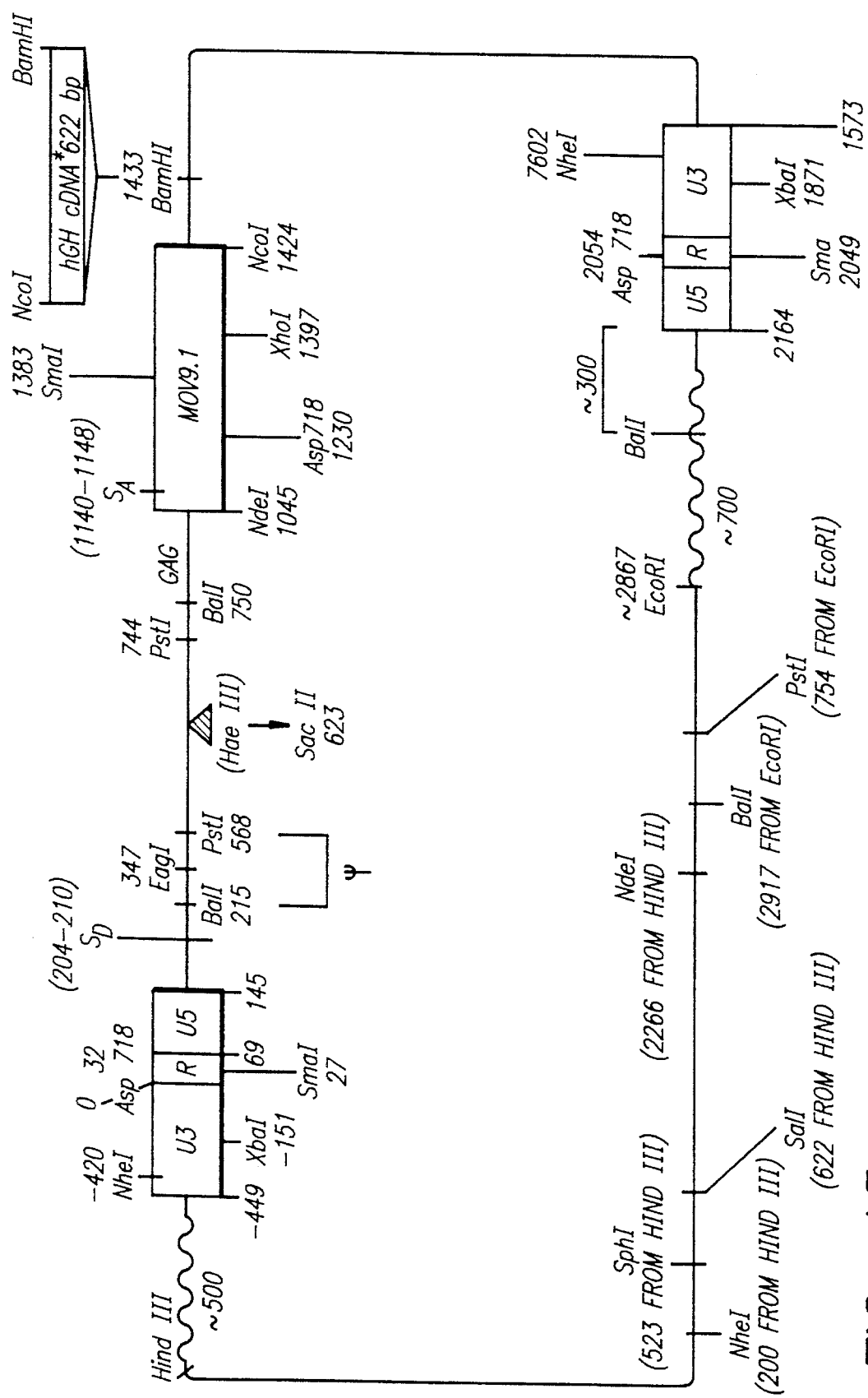

FIG. 15 is a schematic diagram of the retroviral vector α-SGC.

Figure 16A:
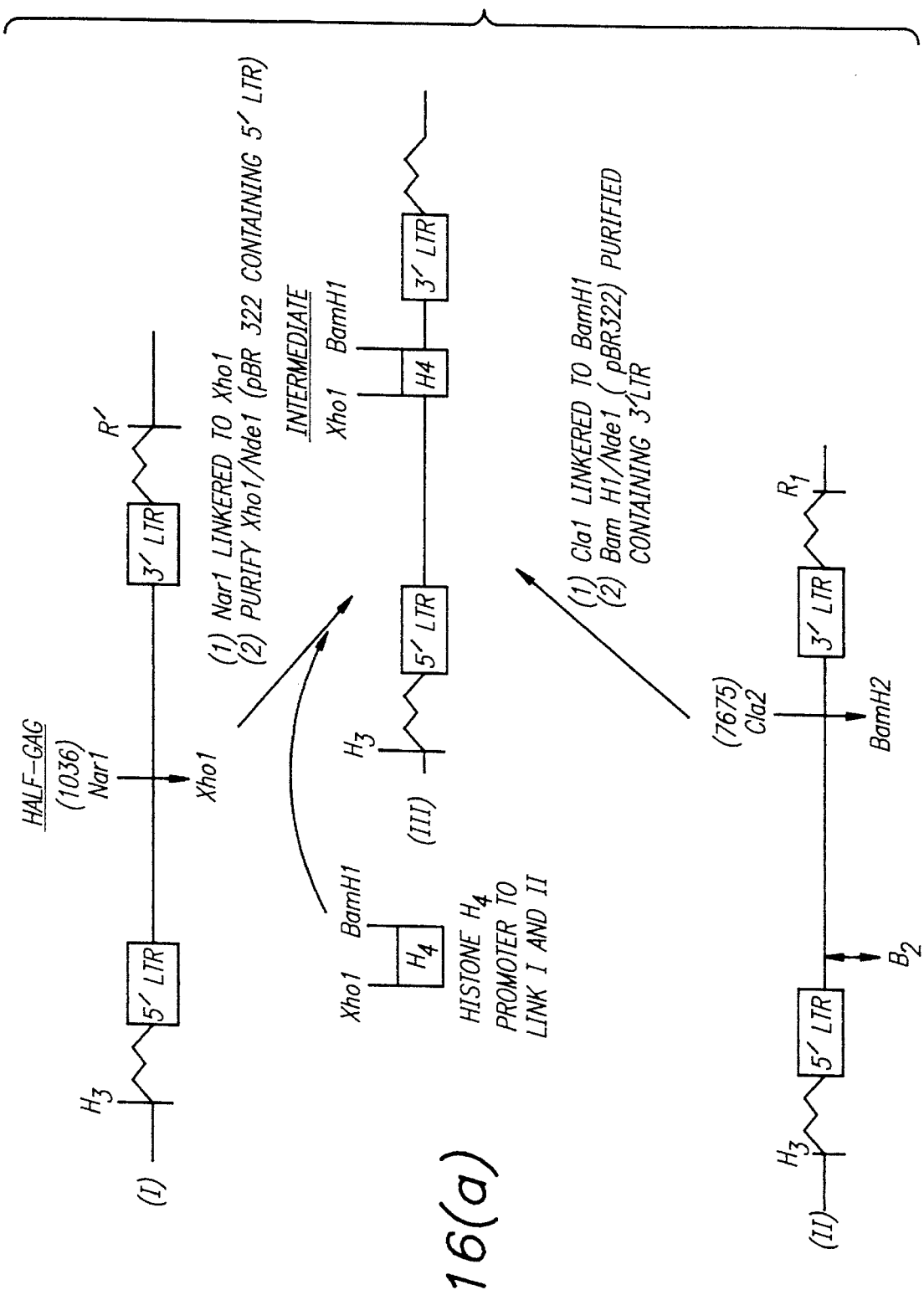
Figure 16B:
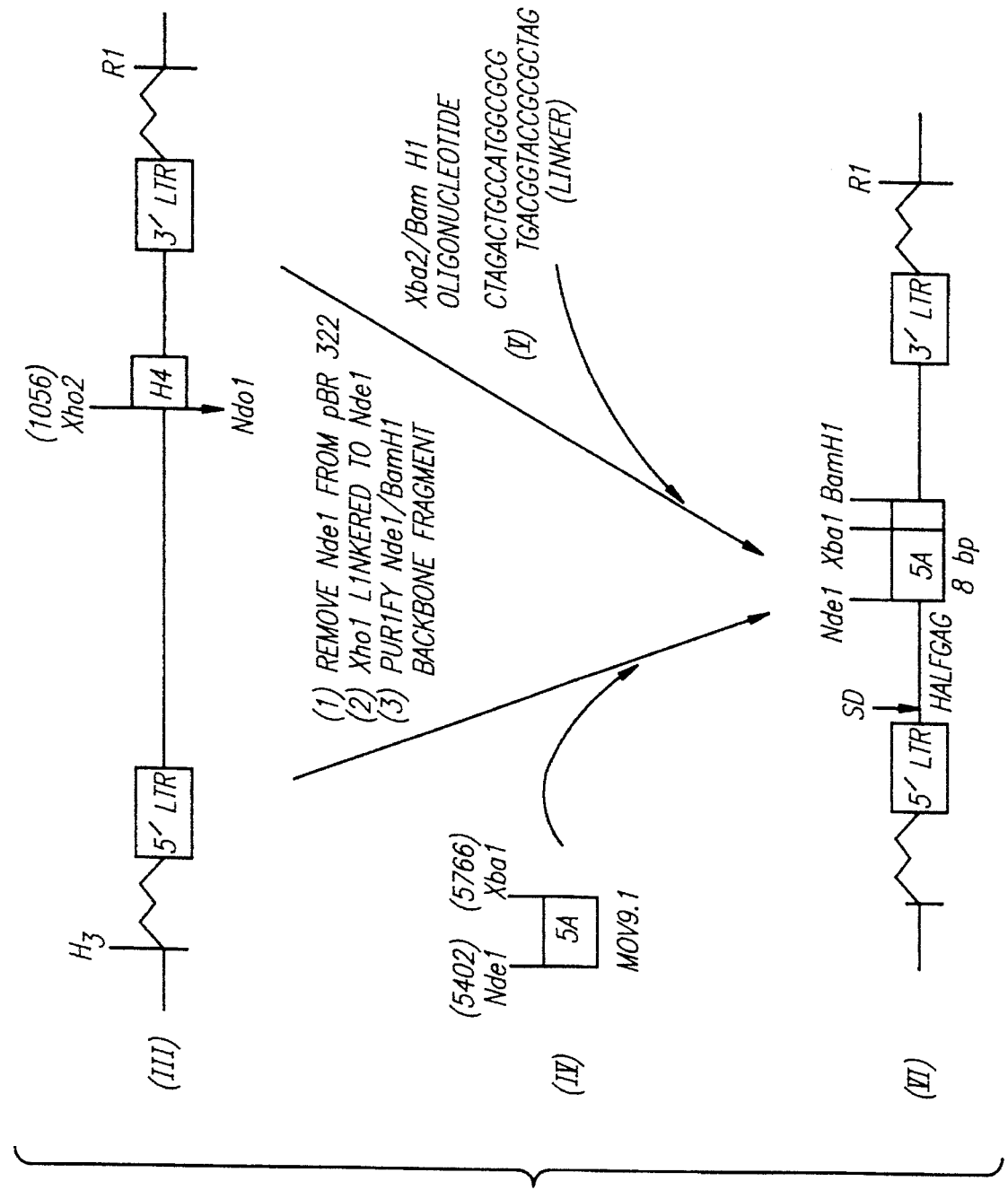

FIGS. 16(a) and 16(b) represents a schematic diagram of the construction of the MFG vector of the invention.

DETAILED DESCRIPTION OF THE INVENTION

The present invention is based on development of an effective method of introducing genetic material of interest into hepatocytes and of a method of transplanting hepatocytes containing the genetic material of interest. Using an appropriate vector, such as a retroviral vector, which includes the genetic material of interest, or other means, it is possible to introduce such genetic material into hepatocytes, where it is expressed. In particular, it has been demonstrated that DNA of interest can be efficiently and stably introduced into mature cultured hepatocytes, which subsequently express the DNA (produce the encoded polypeptide), and that the transduced hepatocytes can be grafted or transplanted. In addition, such a vector can be used to introduce genetic material of interest into hepatocytes in vivo, thus avoiding the need to transplant or graft transduced hepatocytes.

The following is an explanation of isolation of hepatocytes to be transduced ex vivo and grafted or transplanted into a recipient, using the method of the present invention; of vectors useful in introducing genetic material of interest into hepatocytes, either ex vivo or in vivo; and of the method of the present invention by which hepatocytes are transduced.

Isolation of Hepatocytes

In one embodiment of the method of the present invention, cultured mature hepatocytes are transduced and subsequently grafted or transplanted into a recipient. In this embodiment, hepatocytes are obtained, either from the recipient (i.e., the individual who is to receive the transduced hepatocytes) or from a donor, using known techniques. In general, this includes removing all or a portion of a liver, from which hepatocytes are removed by in situ perfusion of a collagenase solution. For example, in the case of isolation of hepatocytes from an intact liver, a catheter is inserted into a vein which either leaves or enters the liver, collagenase solution is perfused through and hepatocytes are released. In the case of a liver biopsy, which results in a cut or exposed surface, a small catheter (or catheters) is inserted into vessels on the open or cut surface. Collagenase solution is perfused through the catheterized vessels, resulting in release of hepatocytes. Once removed or isolated, the hepatocytes are plated and maintained under conditions (e.g., on appropriate medium, at correct temperature, etc.) suitable for transfection.

For example, several methods have been described for isolating highly enriched populations of rat hepatocytes and maintaining these cells in culture for extended periods of time. Koch, K. S. and H. L. Leffert, *Annals N.Y. Academy of Sciences*, 349:111–127 (1980); McGowan, J. A. et al., *Journal of Cellular Physiology*, 108:353–363 (1981); Bissell, D. M. and P. S. Guzelian, *Annals of the New York Academy of Sciences*, 349:85–98 (1981); and Enat, R. et al., *Proceedings of the National Academy of Sciences, U.S.A.*, 81:1411–1415 (1984). Such methods can be used to isolate and maintain hepatocytes to be transduced by the method of the present invention. Hepatocytes can also be prepared using a modification of the procedure developed by Barry and Friend, described below and in Example 1, with the perfusion mixture described by Leffert. Leffert, H. L. et al., *Methods in Enzymology*, 58:536–544 (1979), the teachings of which are incorporated herein by reference.

Retroviral Vectors

One limitation of hepatocyte cultures for studying the molecular aspects of processes such as gene regulation has historically been the lack of efficient gene transfer techniques. Conventional methods of transfection are inefficient and toxic to the cells. Tur-Kaspa, R. *Molecular and Cellular Biology*, 6:716–318 (1986). As described below, recombinant retroviruses have been used to overcome these problems. As a result, it is now possible to efficiently and stably transduce primary cultures of hepatocytes by replication-defective retroviruses. Such replication-defective retroviruses have been used to introduce genetic material of interest into cultured hepatocytes. Transduction is efficient and produces hepatocytes which express the genetic material of interest (i.e., produce the encoded protein or polypeptide) and which retain the ability to be transplanted.

Retroviruses are RNA viruses; that is, the viral genome is RNA. This genomic RNA is, however, reverse transcribed into a DNA intermediate which is integrated very efficiently into the chromosomal DNA of infected cells. This integrated DNA intermediate is referred to as a provirus. As shown in FIG. 1, the retroviral genome and the proviral DNA have three genes: the gag, the pol and the env, which are flanked by two long terminal repeat (LTR) sequences. The gag gene encodes the internal structural (nucleocapsid) proteins; the pol gene encodes the RNA-directed DNA polymerase (reverse transcriptase); and the env gene encodes viral envelope glycoproteins. The 5' and 3' LTRs-serve to promote transcription and polyadenylation of virion RNAs.

Adjacent to the 5' LTR are sequences necessary for reverse transcription of the genome (the tRNA primer binding site) and for efficient encapsidation of viral RNA into particles (the Psi site). Mulligan, R. C., *Experimental Manipulation of Gene Expression*, M. Inouye (ed), 155–173 (1983); Mann, R., et al., *Cell*, 33:153–159 (1983); Cone, R. D. and R. C. Mulligan, *Proceedings of the National Academy of Sciences. U.S.A.*, 81:6349–6353 (1984).

If the sequences necessary for encapsidation (or packaging of retroviral RNA into infectious virions) are missing from the viral genome, the result is a cis defect which prevents encapsidation of genomic RNA. However, the resulting mutant is still capable of directing the synthesis of all virion proteins. Mulligan and coworkers have described retroviral genomes from which these Psi sequences have been deleted, as well as cell lines containing the mutant stably integrated into the chromosome. Mulligan, R. C., *In: Experimental Manipulation of Gene Expression*, M. Inouye (ed), 155–173 (1983); Mann, R., gill, 33:153–159 (1983); Cone, R. D. and R. C. Mulligan, *Proceedings of the National Academy of Sciences. U.S.A.*, 81:6349–6353 (1984). The teachings of these publications are incorporated herein by reference.

The Psi 2 cell line described by Mulligan and coworkers was created by transfecting NIH 3T3 fibroblasts with pMOV-Psi which is an ecotropic Moloney murine leukemia virus (Mo-MuLV) clone. pMOV-Psi expresses all the viral gene products but lacks the Psi sequence, which is necessary for encapsidation of the viral genome. pMOV-Psi expresses an ecotropic viral envelope glycoprotein which recognizes a receptor present only on mouse (and closely related rodent) cells.

Another cell line is the Psi am line, which are Psi-2-like packaging cell lines. These Psi-am cell lines contain a modified pMOV-Psi-genome, in which the ecotropic envelope glycoprotein has been replaced with envelope sequences derived from the amphotropic virus 4070A. Hartley, J. W. and W. P. Rowe, *Journal of Virology*, 19:19–25 (1976). As a result, they are useful for production of recombinant virus with a broad mammalian host range, amphotropic host range. The retrovirus used to make the Psi am cell line has an amphotropic host range and can be used to infect human cells. If the recombinant genome has the Psi packaging sequence, the Psi-am cell line is capable of packaging recombinant retroviral genomes into infectious retroviral particles. Cone, R. and R. Mulligan, *Proceedings of the National Academy of Sciences, USA*, 81:6349–6353 (1984).

The retroviral genome has been modified by Cone and Mulligan for use as a vector capable of introducing new genes into cells. As shown in FIG. 2, the gag, the pol and the env genes have all been removed and a DNA segment encoding the neo gene has been inserted in their place. The neo gene serves as a dominant selectable marker. The retroviral sequence which remains part of the recombinant genome includes the LTRs, the tRNA binding site and the Psi packaging site. Cepko, C. *Cell*, 37:1053–1062 (1984).

Additional vector-constructions which bad be used in producing transduced hepatocytes of the present invention are represented in FIG. 2 and are described in detail below.

pVL. The characteristics of this vector have been described in Korman, A. J. et al., *Proceedings of the National Academy of Sciences, USA*, 84:2150 (1987). This vector is capable of expressing both the gene of interest and a dominant selectable marker, such as the neo gene. The gene of interest is cloned in direct orientation into a BamHI/Smal/SalI cloning site just distal to the 5' LTR, while the Neo gene is placed distal to an internal promoter (from SV40) which is farther 3' than is the cloning site (is located 3' of the cloning site). Transcription from pLJ is initiated at two sites: 1) the 5' LTR, which is responsible for expression of the gene of interest and 2) the internal SV40 promoter, which is responsible for expression of the neogene. The structure of pLJ is represented in FIG. 2a.

Vector pLJ is represented in FIG. 2a. In pLJ, the genetic material of interest is inserted just following the 5' LTR. Expression of this genetic material is transcribed from the LTR and expression of the neo gene is transcribed from an internal SV40 promoter.

pEM. In this simple vector, the entire coding sequence for gag, pol and env of the wild type virus is replaced with the gene of interest, which is the only gene expressed. The components of the pEM vector are described below. The 5' flanking sequence, 5' LTR and 400 bp of contiguous sequence (up to the BamHI site) is from pZIP. The 3' flanking sequence and LTR are also from pZIP; however, the ClaI site 150 bp upstream from the 3' LTR has been ligated with synthetic BamHI linkers and forms the other half of the BamHI cloning site present in the vector. The HindIII/EcoRI fragment of pBR322 forms the plasmid backbone. This vector is derived from sequences cloned from a strain of Moloney Murine Leukemia virus. An analogous vector has been constructed from sequences derived from the myeloproliferative sarcoma virus. The structure of pEM is represented in FIG. 2b.

pIp. This vector is capable of expressing a single gene driven from an internal promoter. The structure of pip is represented in FIG. 2c. The construction of these vectors is summarized below. The 5' section of the vector, including the 5' flanking sequences, 5' LTR, and 1400 bp of contiguous sequence (up to the Xho site in the gag region) is derived from wild type Moloney Leukemia virus sequence. Shinnick et al., *Nature*, 293:543 (1981). The difference between the two is that a SacII linker is cloned into an HaeIII restriction site immediately adjacent to the ATG of the gag gene. The 3' section of the vector, including the 3' flanking sequences, 3' LTR and 3' contiguous sequence (up to the ClaI site in the env coding region) is from pZIP. However, there are two modifications: 1) the ClaI site has been linked to BamHI and 2) a small sequence in the 3' LTR spanning the enhancer (from PvuII to XbaI) has been deleted. Bridging the 5' and 3' sections of the vector is one of several promoters; each one is contained on a XhoI/BamHI fragment, and each is capable of high level constitutive expression in most tissues. These promoters include beta-actin from. chicken (Choudory, P. V. et al., CSH Symposia *Quantitative Biology*, L. I. 1047 (1986), and thymidine kinase from Herpes Simplex Virus, histone H4 from human (Hanly, S. M. et-al., *Molecular and Cellular* 5:380 (1985)). The vector backbone is the HindIII/FcoRI fragment from pBR322. The gene of interest is cloned into the BamHI site in direct orientation, just downstream from the internal promoter.

Vectors without a selectable marker can also be used to transduce endothelial cells with genetic material of interest. Such vectors are basically simplifications of the vectors previously described, in which there is such a marker. Vector pEM is represented in FIG. 2b; as represented, the main components of the vector are the 5' and 3' LTR, and the genetic material of interest, inserted between the two LTRs. Retroviral vectors useful for ex vivo modification of hepatocytes Four additional recombinant retroviruses suitable for introducing genetic material of interest into cultured hepatocytes and expressing biologically significant amounts of the encoded protein or polypeptide are also represented in FIG. 3, with specific reference to the human LDLR gene. These vectors, which included the human LDLR gene, have been used to efficiently transduce hepatocytes, which then expressed levels of LDLR equal to normal endogenous levels. These vectors will be illustrated with reference to the LDLR gene, but any nucleotide sequence of interest can be incorporated into the retroviruses and introduced into hepatocytes.

As shown, each vector differs in the transcriptional elements used to drive expression of the gene. These are described in detail in Example IV. Briefly, in the vector LTR-LDLR, transcription should begin at the 5' LTR, with the result that a single full length viral transcript, in this case, one which expresses LDLR, is produced. In the remaining vectors, expression of LDLR should be driven by transcripts initiated from transcriptional control sequences located internal to the proviral transcriptional unit.

Each of these latter vectors differs in the transcriptional elements responsible for transcription: BA-LDLR contains the promoter from chicken beta-actin gene; H4-LDLR contains the promoter from the human histone H4 gene; and TK-LDLR contains the promoter from the thymidine kinase gene from herpes simplex virus. Each of the three vectors also contains a deletion of viral transcriptional enhancer sequences located in the 3' LTR, in order to reduce the amount of viral transcription which occurs after reverse transcription and integration of the recombinant provirus. Human LDLR coding sequences for all four vectors were derived from a full length human LDLR cDNA insert.

As described in Example IV, use of these vectors in transducing hepatocytes resulted in levels of viral-directed LDLR RNA in the transduced cells that exceeded endogenous levels (50–100×). The amount of functional receptor produced, however, was less than or equal to normal endogenous levels for most vectors, possibly due to insufficient RNA processing or transport or diminished translational efficiency. Because a potential problem with the ex vivo method of hepatocyte modification is the fact that only a fraction of the total hepatocytes isolated can be engrafted, additional retroviral vectors that express higher levels of the encoded protein (here, LDLR) may be useful. Such vectors may be useful, for example, as a means of decreasing the number of transplanted cells required for production of useful quantities of the encoded protein. For example, each vector can include specialized transcriptional control sequences which are internal to the proviral transcriptional unit. This makes it possible to provide variation in the level of transcription of the nucleotide sequence of interest. Of particular interest here are transcriptional elements from genes expressed at high levels in liver cells (e.g., alpha-fetoprotein, albumin).

To enhance the translational efficiency of the chimeric nucleotide sequence of interest RNAs generated by the vectors, (e.g., by generating more translatable RNAs), selected 5' and 3' nontranslated sequences from a well-characterized gene (e.g., RU-5 region of a human retrovirus) or the authentic 5' and 3' nontranslated sequences of the nucleotide sequence of interest can also be included in the retroviral vectors used.

Because it is possible that constitutive production of very high levels of the encoded protein (e.g., LDLR) may result in toxicity to cells, it may also be appropriate to include in the vector sequences from the nucleotide sequence of interest (or gene) which confer transcriptionally-mediated end-product repression. For example, in the case of the LDLR gene, sequences (called the steroid responsive elements) which confer transcriptionally-mediated, end-product repression by sterols can be included in the vector.

Retroviral vectors for in vivo modification of hepatocytes

It is also possible to use vectors, particularly recombinant retroviral vectors, to transduce hepatocyte cells in vivo. For example, one strategy for targeting the LDLR gene to hepatocytes can be based on the presence of the asialoglycoprotein (ASGP) receptor on hepatocytes. This receptor, which is specifically expressed in hepatocytes, is involved in the uptake and catabolism of glycoproteins that have had their terminal sialic acids removed, thereby exposing penultimate galactose residues. Glycoprotein-receptor complexes are internalized by receptor mediated endocytosis. Asialoglycopeptideprotein conjugates and asialoglycopeptide-coated vesicles have been used to specifically deliver a variety of bioactive agents to the liver in vivo. Aitie, A. D. et al., *Proceedings of the National Academy of Sciences, USA*, 27:5923–5927 (1980); Fiumw, L. et-al., *FEBS Letter*, 103:47–51 (1979); Hildenbrandt, G. R. and N. N. Aronson, *BBA*, 631:499–502 (1980).

For example, one approach to targeting delivery of genes to hepatocytes can be based on the modification of existing retroviruses to make them ligands for the ASGP receptors. The envelope proteins from murine leukemia viruses are complex glycoproteins that have a high content of sialic acid. Internalization of virus occurs through the specific interaction of the viral envelope with a cell surface receptor, followed by receptor-mediated endocytosis of the virus/receptor complex.

Hepatocyte-specific transduction may be possible if modified virions that are specifically internalized by the ASGP receptor are developed and used. For example, it is possible to use viruses whose envelope protein is devoid of sialic acid, thereby rendering them ligands for the ASGP receptor. One approach is to enzymatically remove the terminal sialic acids from intact virions with neuraminidase. Alternatively, it is possible to construct viral producer lines with genetically modified envelope genes that code for glycoproteins with terminal galactose residues. It is possible to construct chimeric envelope genes that encode fusion proteins in which the carboxy terminal sequences are derived from the 3' portion of the envelope gene and the amino terminal sequences are derived from genes of known ligands for ASGP receptor. In addition, it is possible to use lectin-resistance selection systems to isolate mutants of the viral producer lines that are incapable of adding terminal sialic acids to N-linked chains. Viruses produced from these lines should bind to the ASGP receptor. Transduction of cells that express ASGP receptor with these modified virions can be tested in vitro and in vivo.

Another approach to the targeted delivery of genes to hepatocytes has recently been described by Wu, Wu, G. Y. and C. H. Wu, *Journal of Biological Chemistry*, 262:4429–4432 (1987). Wu coupled pSV2CAT plasmid to a ligand of the ASGP receptor called asialoorosomucoid (ASOR) and demonstrated in HEP G2 cells uptake of the conjugates via the ASGP receptor and expression of CAT activity. After administration of this conjugate to rats, specific, but transient, expression of CAT was demonstrated in liver homogenates. It is possible that this method can be modified to produce a method by which recombinant retroviral vectors or episomal vectors can be introduced into hepatocytes vivo. The efficiency and specificity of this delivery system can be assessed, for example, by transferring an expression vector that stably expresses a product which can be detected in situ by direct analysis of the product (e.g., beta-galactosidase).

Successful application of in vivo targeting requires stable expression of the transferred gene. Transduction of hepatocytes in vivo with retroviruses that have been modified to allow for uptake via the ASGP receptor will require integration of the provirus into genomic DNA. Integration is rare in the quiescent liver, however. The efficiency of retroviral integration may be improved by exposing the recipient to virus following partial hepatectomy. During this time, the residual hepatocytes undergo rapid proliferation. This, however, may not be practical clinically. One way to avoid this problem is to modify the retroviral vector in such a way as to promote its persistence as an episome in the form of a double stranded DNA circle. This can be done by incorporating the cis (oriP) and trans (EBNA) sequences of Epstein Barr Virus that are required for plasmid replication into a retrovirus vector. It is also possible to use other sequences (called autonomously replicating sequences) isolated from the eukaryotic (e.g., mouse) genome which have been shown to drive the autonomous replication of plasmids. In these cases, vectors containing deletions of sequences within the inverted repeats of the long terminal repeats which prevent proviral integration into the host chromosome, will be used.

Of particular interest for use in the in vivo modification of hepatocytes are the retroviral vectors MFG (ATCC no. 68754) and α-SGC (ATCK no. 8755). These vectors can be used to produce recombinant viruses having titers that are high enough to obviate the need for selective pressure when used when used in vivo. MFG and in α-SGC are described in detail in PCT application PCT/US91/08121 filed Oct. 31, 1991.

Introduction of Genetic Material into Hepatocytes

Genetic material of interest has been incorporated into cultured hepatocytes and expressed in the resulting genetically engineered hepatocytes, as described below and in the examples.

Genetic material which can be incorporated into hepatocytes according to the method described can be: 1) genetic material (DNA or RNA) which is present in and expressed at biologically effective levels (levels sufficient to produce the normal physiological effects of the polypeptide it encodes) in normal hepatocytes, but present in or expressed in less than normal quantities in the hepatocytes prior to stable transfer of genetic material of interest into them by the method of the present invention; 2) genetic material not present in normal hepatocytes; or 3) genetic material present in normal hepatocytes but not expressed at biologically effective levels in such cells, alone or in any combination thereof. Hepatocytes in which genetic material (DNA or RNA) is present in or expressed in less than normal quantities are referred to herein as genetically deficient hepatocytes.

The genetic material incorporated into and expressed by hepatocytes can also, optionally, include genetic material encoding a selectable marker, thus making it possible to identify and select cells which contain and express the genetic material of interest.

Thus, DNA or RNA introduced into cultured hepatocytes of the present invention includes the genetic material (DNA or RNA) of interest and, optionally, genetic material encoding a selectable marker; such DNA or RNA is referred to as incorporated genetic material (or incorporated DNA, incorporated RNA). Hepatocytes containing incorporated genetic material are referred to as transduced hepatocytes; they express the DNA or RNA of interest and produce the encoded protein or polypeptide.

Exogenous DNA encoding a polypeptide or protein of interest and, optionally, a selectable marker (e.g., neo, which encodes neomycin resistance) is incorporated in vivo into hepatocytes as described below and in Examples I–III. Hepatocytes isolated as described previously are plated at subconfluent density on matrix substrata and maintained in hormonally defined media, such as that described by Enat, et al., the teachings of which are incorporated herein by reference. Enat, R., et al., *Proceedings of the National Academy of Sciences, USA,* 81:1411–1415 (1984). The media is changed as needed to maintain the hepatocytes.

Cells are subsequently infected with an amphotropic retrovirus which contains DNA of interest (e.g., DNA encoding a polypeptide whose expression in hepatocytes is desired) and, optionally, DNA encoding a selectable marker to be incorporated into the hepatocytes. The hepatocytes are infected with the recombinant retrovirus (and thus transduced with the DNA of interest) by exposing them to virus which has a recombinant genome. This results in infection of the cells by the recombinant retrovirus. It is possible to optimize the conditions for infection of the hepatocytes by using a high titer amphotropic virus.

A cell line which produces recombinant amphotropic retrovirus having a recombinant genome is used to infect hepatocytes. The recombinant genome can include a variety of components, but in general is comprised of two LTRs and, in place of the gag, the pol and the env sequences, a second promoter sequence; in some cases, it also includes a gene encoding a selectable marker (e.g., neo).

Viral stocks, to be used in introducing genetic material of interest into hepatocytes, are harvested, as described above, supplemented with Polybrene (Aldrich) and added to the culture of hepatocytes. If the titer of the virus is high (e.g., approximately $10^6$ cfu per ml), then virtually all hepatocytes will be infected and no selection of transduced hepatocytes is required. If the titer is very low, then it is necessary to use a retroviral vector that has a selectable marker, such as neo or his. If a selectable marker is used, after exposure to the virus, the cells are grown to confluence and split into selective media (e.g., media containing G418 if the selectable marker is neo, media containing histidinol and no histidine if the selectable marker is his). The neo gene is a bacterial gene derived from the transposon Tn5, which encodes neomycin resistance in bacteria and resistance to the antibiotic G418 in mammalian cells. This neo gene acts as a dominant selectable marker; its presence in a mammalian cell converts the cell into one which will grow in the presence of G418. (If it is not present, the cell dies in the presence of G418.) As a result, the presence of this gene in a mammalian cell can be determined by culturing cells in media which contains G418.

The recombinant retroviral vectors having the neogene also have a cloning site. As a result, genetic material of interest can be introduced into the vector, incorporated into hepatocytes and expressed by hepatocytes transduced with the recombinant retrovirus (referred to as hepatocytes containing incorporated genetic material). At the BamHI cloning site, it is possible to insert genetic material of interest. As described above, hepatocytes have been transduced with the gene encoding beta-galactosidase from *E. coli*. The efficiency of transduction was assessed, as described in Example III. Expression of the beta-galactosidase gene was also assessed and is detailed in Example III.

For example, a helper-free amphotropic producer is grown in tissue culture to a confluent density in Dulbecco's Modified Eagle's Medium (DME) supplemented with 10% calf serum (CS). Fresh media is added and subsequently the media is harvested. The spent media (or viral stock) is filtered to remove detached producer cells and is used immediately to infect cells or is stored (e.g., at –70° C.) for later use.

Media is removed from a subconfluent plate of hepatocytes (recipient hepatocytes) and quickly replaced with viral stock which contains Polybrene (Aldrich). Subsequently, this is removed and replaced with fresh media. Thus, the media used is a viral supernatant and the recombinant genome of the infectious virus includes DNA of interest. The infection procedure results in hepatocytes which express the DNA encoding a gene product of interest and, optionally, a selectable marker.

In one embodiment, hepatocytes are exposed to media containing infectious virus produced in Psi am cells; the infectious virus contain a recombinant genome having the genetic material of interest. The recombinant genome in one instance includes genetic material encoding a protein or a polypeptide (e.g., the receptor for low density lipoproteins; ornithine transcarbalyase) and, optionally, a gene encoding a dominant selectable marker (e.g., the neo gene which encodes neomycin resistance). As a result, the hepatocytes are transduced—that is, the genetic material of interest (for example, DNA encoding a polypeptide or a protein of interest) and, optionally, the neogene are stably introduced into the hepatocytes. The transduced hepatocytes express the encoded protein or polypeptide and, if the neogene is present, express it, resulting in cells having the selectable trait.

One embodiment of the present invention is described in detail in the Examples. Briefly, hepatocytes were prepared using a modification of the method of Berry and Friend with the perfusion mixture of Leffert. Berry, M. N. et al., *J. Cell. Biol.*, 43:506–520 (1969); Leffert, H. L. et al., *Methods Enzymol.*, 58:536–644 (1979). The resulting hepatocytes were plated at a density of 3–4×10$^4$ cells/cm$^2$ onto Primaria plates substratum in hormonally defined media supplemented with 10% fetal bovine serum. The media was replaced with fresh hormonally defined media, which was subsequently changed periodically. Spent media was obtained by harvesting DME media supplemented with 10% calf serum in which a helper-free amphotropic producer of the BAG virus was cultured. Conditions for infection of the hepatocytes were optimized through the use of BAG, which is a high titer amphotropic virus encoding *E. coli* beta galactosidase. The producer coexpressed beta-galactosidase from *E. coli* and the bacterial neogene. The spent media was filtered to remove detached producer cells and used as viral stock to infect hepatocytes.

Cells were infected by removing media from a subconfluent plate of hepatocytes (recipient hepatocytes) and replacing it with viral stock. Hepatocyte cultures were infected in this way for approximately 12 hours. Hepatocytes containing the DNA of interest (i.e., DNA encoding beta-galactosidase) and the neogene were isolated by culturing on media containing the antibiotic G418. Those into which the recombinant retrovirus was effectively introduced by infection, referred to as transduced hepatocytes, produce beta-galactosidase and are neomycin resistant. The ability of hepatocytes transduced with the recombinant retrovirus having the beta-galactosidase gene to produce beta-galactosidase has been assessed in vitro. This assessment is described in Example III.

Rat hepatocytes have also been transduced with the gene encoding human parathyroid hormone (hPTH) and shown to express the encoded hormone. This is described in Example VI and results are presented in FIG. 9.

As a result, it has been demonstrated that transduced hepatocytes secrete a polypeptide (betagalactosidase) which is normally not secreted by hepatocytes. A similar approach can be used to introduce any genetic material into hepatocytes in such a manner that the encoded product is made and to assess expression of the incorporated genetic material.

For example, hepatocytes have been transduced as a result of exposure to media containing infectious virus in which the recombinant genome includes DNA encoding human LDLR. This is described in detail in Example IV. Hepatocytes were infected with four LDLR virus preparations (each including one of the vectors represented in FIG. 5) and subsequently analyzed for gene transfer and LDLR expression.

The same vectors can be used in the method of the present invention, to introduce into cultured hepatocytes any nucleotide sequence or gene of interest. Alternatively, other vectors can be used, as can other means of introducing genetic material of interest into cultured hepatocytes.

As explained previously, it may also be possible to introduce genetic material of interest into hepatocytes in vivo. As described, a recombinant retrovirus in which the genome includes the genetic material of interest would be targeted to hepatocytes, with the result that after introduction-into an individual's body (e.g., by intravenous injection), the retrovirus is specifically taken up by hepatocytes. Once taken up by hepatocytes, the recombinant retroviral genome will be expressed, resulting in production of the protein or polypeptide encoded by the genetic material of interest. Preferably, the virus used to introduce the genetic material of interest is podified (e.g., through inclusion of sequences, referred to as autonomously replicating sequences or ARS) in such a manner that integration of the provirus into the host chromosomes does not occur. As a result, replication will occur episomally.

Use of Dominant Selectable Markers-in the Introduction of Genetic Material Encoding Polypeptides In addition to genetic material of interest, a vector can include genetic material encoding a selectable marker, the presence of which makes it possible to identify and select for cells transduced with the genetic material of interest. As described previously and in Example III, the neogene, which is such a marker, has been used for this purpose. It is also possible to use dominant selectable markers other than the neogene to introduce genetic material into hepatocytes. For example, the His D gene can be used for this purpose. The His D gene is a bacterial gene from *Salmonella typhimurium* and encodes histidinol dehydrogenase, a polypeptide which converts histidinol to histidine. Histidine is an essential amino acid; histidinol is an alcohol analogue of histidine and can be converted to histidine under the proper metabolic conditions. If cells are grown in media containing histidinol but lacking histidine, those cells having the His D gene can convert histidinol to histidine. Because histidine is essential to their function, those cells which have the His D gene (and thus can make histidine) will survive and those lacking the gene will not.

A retrovirus vector having the His D gene has been used to infect keratinocytes. The keratinocytes containing His D gene were selected by growing these cells in media lacking histidine but containing histidinol. As expected, keratinocytes having the His D gene formed colonies and grew to confluence; those lacking the gene did not. In fact, such cells occurred at a much higher frequency than those in which the neogene was included. These same techniques are useful in selecting fibroblasts containing DNA of interest.

As a result of this work, it is also possible to use independent dominant selectable markers (e.g., the neo gene and the His D gene) to introduce more than one type of new genetic material into hepatocytes. In the case of gene products which have two different subunits, for example, separate dominant selectable markers can be used to introduce the genetic information encoding the two subunits. In addition, two or more dominant selectable markers can be used in the case of gene products which need to be specifically cleaved or processed in order to become active. A gene encoding the necessary processing enzyme can be introduced along with the gene encoding the polypeptide requiring such processing. This would enable hepatocytes to process the polypeptide hormone.

Other vehicles for the Introduction of Genetic Material of Interest into Hapatocytes It is also possible to use vehicles other than retroviruses to genetically engineer or modify hepatocytes. Genetic information of interest can be introduced by means of any virus which can express the new genetic material in such cells. For example, SV40, herpes virus, adenovirus and human papilloma virus can be used for this purpose. DNA viruses can also be used to introduce genetic material of interest, as well as a gene encoding a selectable marker, into hepatocytes according to the method of the present invention.

Transplantation of Transduced Hepatocytes

Hepatocytes expressing the incorporated genetic material are grown to confluence in tissue culture vessels; removed from the culture vessel; and introduced into the body. This can be done surgically, for example. In this case, the tissue which is made up of transduced hepatocytes capable of expressing the nucleotide sequence of interest is grafted or transplanted into the body. For example, it can be placed in the abdominal cavity in contact with/grafted onto the liver or in close proximity to the liver. Alternatively, the transduced hepatocyte containing tissue can be attached to microcarrier beads, which are introduced (e.g., by injection) into the peritoneal space of the recipient. This approach has been shown to be successful by transplantation of wild type hepatocytes into a strain of rats (Nagase analbuminemic rats) which are deficient in albumin synthesis and demonstration of moderate levels of albumin in serum of transplanted animals. Direct injection of genetically modified hepatocytes into the liver may also be possible.

Once introduced into the body of an individual, the transduced hepatocytes provide a continuous supply of the hormone, enzyme or drug encoded by the genetic material of interest. The amount of the hormone, enzyme or drug supplied in this way can be modified or regulated as needed (e.g., by using external cues or factors which control or affect production, by controlling the size of the graft or the quantity of fibroblasts introduced into the body, or by removing the graft).

Genetically modified hepatocytes have been implanted into WHHL rabbits, which lack LDL receptor function. As described in Example V, and animal model of familial hypercholesterolemia was used to develop a new therapeutic approach in which a normal LDL receptor gene is introduced into genetically deficient hepatocytes, which are transplanted into recipients. Homozygous familial hypercholesterolemia is a life threatening disorder for which no effective medical therapy exists (Goldstein, J. L. and M. S. Brown, in *The Matabolic Basis of Inherited Disease*, eds. Scriver, C. R., Beaudeut, A. L., Sly, W. S. & Valle, D. (McGraw-Hill, Inc.), pp. 1215–1250 (1989)). The strategy described in Example V involves isolating hepatocytes from an animal, transducing a functional LDL receptor gene into these cells in vitro, and transplanting the genetically modified cells into another animal of the same type.

Use of Genetically Modified Hepatocytes Having Incorporated Genetic Material

The present invention makes it possible to genetically engineer hepatocytes in such a manner that they produce a gene product (e.g., a polypeptide or a protein) of interest in biologically significant amounts. The hepatocytes formed in this way can serve as a continuous drug delivery system to replace present regimens, which require periodic administration (by ingestion, injection, etc.) of the needed substance.

Incorporation of genetic material of interest into hepatocytes would be particularly valuable in the treatment of inherited disease and the treatment of acquired disease. In the case of inherited diseases, this approach is used to provide genetically modified hepatocytes which contain DNA encoding a protein or polypeptide which an individual's hepatocytes are unable to make correctly. For example, this could be used in treating urea cycle disorders. Hepatocytes of the present invention can also be used in the treatment of genetic diseases in which a product (e.g., LDL receptor) normally produced by the liver is not produced or is made in insufficient quantities. Here, hepatocytes transduced with a DNA encoding the missing or inadequately produced substance can be used to produce it in sufficient quantities. In this case, the transduced hepatocytes would produce LDL receptor and thus provide a means of preventing or treating familial hypercholesterolemia, which is an inherited disease in which the primary genetic defect is an abnormality in the expression or function of the receptor for low density lipoproteins. This leads to elevated levels of serum cholesterol and the premature development of coronary artery disease. The transduced hepatocytes could be used to produce sufficient quantities of the LDL receptor to overcome the underlying defect.

There are also acquired diseases for which treatment can be provided through use of genetically engineered hepatocytes. For example, such cells can be used in treating the coagulopathy associated with liver failure. In this case, hepatocytes having incorporated in them a gene encoding one or more clotting factors would correct the acquired deficiency of these factors which leads to bleeding. It may also be possible to treat viral hepatitis, particularly hepatitis B or nonA-nonB hepatitis, by gene transfer. For example, using the method of the present invention, a gene encoding an anti-sense gene could be introduced into hepatocytes to inhibit vital replication. In this case, a vector including a structural hepatitis gene in the reverse or opposite orientation would be introduced into hepatocytes, resulting in production in transduced hepatocytes of an anti-sense gene having the correct orientation.

The present invention will now be illustrated by the following examples, which are not to be seen as limiting in any way.

EXAMPLE I

Hepatocyte Isolation and Culture

Rat hepatocytes were prepared by the procedure of Berry and Friend, using the perfusion mixture of Leffert. Berry, M. N. and D. S. Friend, *Journal of Cell Biology*, 43:506–520 (1969); Leffert, H. L. et al., *Methods in Enzymology*, 58:536–544 (1979). Male Sprague-Dawley rats weighing between 200 and 250 gms were used as the source of hepatocytes. Cells were plated at a density of $4 \times 10^4$ cells/$cm^2$ onto one of several matrix substrata in hormonally defined media supplemented with 10% fetal bovine serum. Enat, R. et al., *Proceedings of the National Academy of Sciences, USA*, 81:1411–1415 (1984). Four hours later the media was replaced with fresh hormonally defined media which was subsequently changed every 24 hours during the duration of the experiment. The following substrata were used: 1) Tissue culture plastic—Primaria plates from Falcon Co. were used without additional preparation; 2) Type I collagen—10 cm tissue culture dishes were coated with type I collagen prepared from rat tail tendons. Michalopoulos, G. and H. Pitot, *Exp. Cellular Research*, 94:70–78 (1975). Briefly, collagen was solubilized in 0.1% acetic acid (3 mg/ml) and applied to plates (1 ml/10 cm plate) which were exposed to $NH_3$ vapors, air dried, sterilized by gamma irradiation (10,000 rads), and hydrated with media; 3) Laminin—Purified laminin from Collaborative Research Inc.

(Waltham, Mass.) was applied to tissue culture plates according to the recommendations of the manufacturer; 4) Type IV collagen—10 cm dishes coated with purified type IV collagen were kindly provided by Dr. L. M. Reid (Albert Einstein College of Medicine).

EXAMPLE II

Virus Preparation and Hepatocyte Infection

A helper-free amphotropic producer of the BAG virus was provided by Dr. C. Cepko (Harvard). The retroviral vector used to make this producer has been described by Cepko and co-workers. Price, J., *Proceedings of the National Academy of Sciences, USA*, 84:156–160 (1987). It coexpressed beta-galactosidase from *E. coli* and the bacterial gene that confers resistance to neomycin in prokaryotes and to G418 in eukaryotes (neo). The producer was maintained in Dulbecco's modified Eagle's Medium supplemented with 10% calf serum. Unconcentrated viral stocks were prepared and titered as described by Mann. Mann, R. gill, 33:153–159 (1983). Titers ranged from $1-4 \times 10^5$ cfu/ml. Hepatocyte cultures were infected for 12 hours with vital stocks (5 ml of viral stock/10 cm plate of hepatocytes) containing 8 µg/ml of Polybrene (Aldrich). Transduction efficiency was optimized with respect to the time of exposure to virus and the matrix substrate on which the hepatocytes were plated.

EXAMPLE III

Assessment of Efficiency of Transduction

The efficiency of transduction was initially assessed by directly measuring the integration of provirus.

Southern Analysis

High-molecular-weight cellular DNA from transduced cultures of hepatocytes was isolated as described previously. Maniatis, T. et al., *Molecular Cloning: A Laboratory Manual*, Cold Spring Harbor Laboratory, Cold Spring Harbor, N.Y. (1982). Aliquots (7.5 µg) were digested with the restriction endonuclease Kpn I. Kpn I has recognition sites in the proviral long terminal repeats; consequently, each integrated provirus will be contained in a 6.9 Kb restriction fragment, irrespective of the site of integration.

The restriction fragments were resolved by electrophoresis in 1% agarose gels and analyzed according to the method of Southern using standard procedures and a probe that is complementary to sequences unique to the provirus (i.e., the neogene). Maniatis, T. et al., *Molecular Cloning: A Laboratory Manual*, Cold Spring Harbor Laboratory, Cold Spring Harbor, N.Y. (1982). The blot was probed with the BamHI/Hind III fragment of the neomycin gene that was labelled to high specific activity with 32P-dCTP using the random primer method. Feinberg, A. P. and B. Vogelstein, *Anal. Biochemistry*, 132:6–13 (1983). The intensity of the resulting band on the autoradiograph is proportional to the number of provital integrants in the population.

Figure 4A:
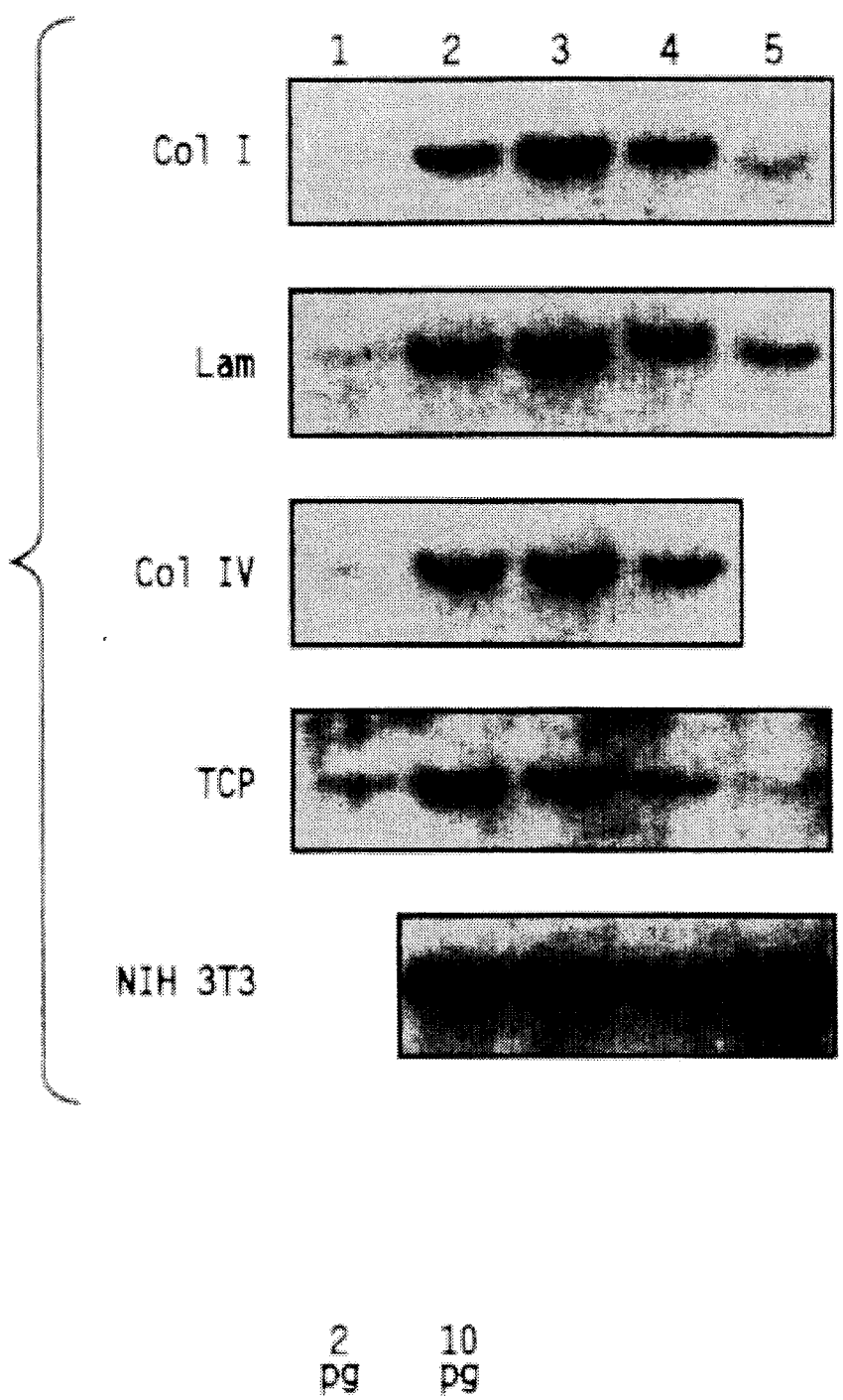
FIGS. 4A–4B is a three-day exposure of a Southern blot in which the effect of extracellular matrix and the time of infection on-integration of provirus in rat hepatocyte cultures are shown.
Figure 4B:
Figure 5C:
FIGS. 5A–5K represents (panels A–F) cytochemical localization of beta-galactosidase activity in transduced cultures of rat hepatocytes and NIH3T3 cell and (panels G–K) liver-specific cytochemical and immunocytochemical stains of rat hepatocyte cultures.
Figure 5F:
Figure 5B:
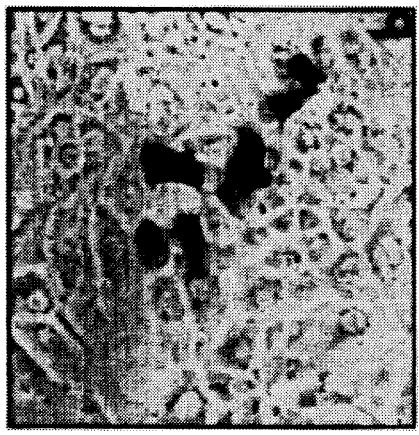
Figure 5E:
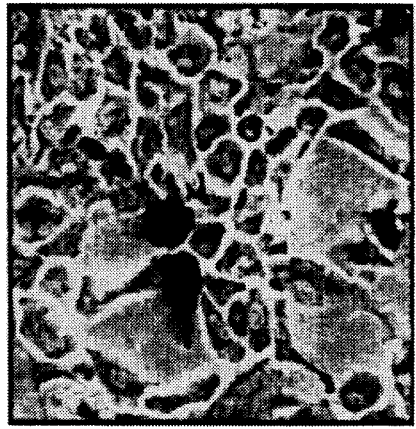
Figure 5A:
Figure 5D:
Figure 5I:
Figure 5H:
Figure 5K:
Figure 5G:
Figure 5J:
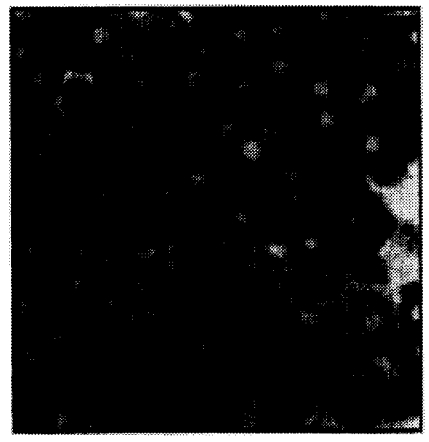

FIG. 4 shows the effect of extracellular matrix used and of the time of infection on integration of provirus in hepatocyte cultures. Panel A presents a Southern blot of hepatocytes isolated from a single collagenase perfusion which were cultured on 10 cm. plates coated with one of several forms of matrix substrata (type I collagen, laminin, type IV collagen, and tissue culture plastic) and infected on days 1, 2, 3, 4, or 5. Infection was carried out using fresh preparations of viral stocks and plates were analyzed for copy number of integrated provirus 48 hours after the infection was initiated. A three day exposure of a Southern blot is shown. A single band was visualized in each lane; the area of the autoradiograph containing this band is shown. Lanes 1–5 indicate the days that the cells were infected. The top four series of bands represent hepatocytes cultured on different forms of matrix: Col I—type I collagen, Lam-laminin, Col IV—type IV collagen, and TCP-tissue culture plastic. The bottom series of bands shows an identical analysis of NIH3T3 cells infected with the same viral stocks used to infect the hepatocyte cultures.

Hepatocytes on each matrix substrata exhibited a consistent pattern of susceptibility to transduction; proviral integration increased from virtually undetectable on day 1 to maximal on days 2 or 3, and subsequently diminished to low levels by day 5. Maximal proviral integration, which was essentially independent of matrix, occurred when cultures were infected on day 2 for cells on tissue culture plastic, or day 3 for cells on type I collagen, laminin, or type IV collagen.

NIH3T3 cells were infected with the same viral stocks used to infect hepatocytes (FIG. 1, panel A). Southern analysis demonstrated little variation in the titer of the viral stocks; the estimated proviral copy number ranged from 0.5 to 0.7 copies/cell. This estimate of copy number was based on a comparison with samples with known quantities of standard plasmid (FIG. 4, panel B) and the assumption that NIH3T3 cells are hypotetraploid.

The samples with known quantities of standard plasmid were made by mixing varying amounts (2 pg and 10 pg) of the purified BAG plasmid with 7.5 µg of uninfected NIH3T3 DNA. Analysis showed a single band, which comigrated with the bands shown in panel A. The data from panels A and B were derived from a three day exposure of the same Southern blot. It was estimated that 2 pg and 10 pg of plasmid in 7.5 µg of NIH3T3 DNA correlates to approximately 0.3 and 1.2 copies of provirus/cell, respectively. The estimated copy number of proviral integrants in maximally infected hepatocytes (e.g., FIG. 4, Lam, lane 3) is approximately 0.2 copies/cell, assuming that the DNA content of NIH3T3 cells is equal to that of hepatocytes. This assumption is probably valid since the majority of hepatocytes in culture are either tetraploid or octaploid. Tomita, Y., *Exp. Cell Res.*, 135:363–370 (1981).

Cytochemical and Immunocytochemical Procedures

A series of liver-specific cytochemical and immunochemical stains was used to document the cellular composition of the hepatocyte cultures. All analyses were performed on three day old cultures of hepatocytes plated on type I collagen.

Cells infected with the BAG virus constitutively produce high levels of cytoplasmic beta-galactosidase. Price, J. et al., *Proceedings of the National Academy of Sciences. U.S.A.*, 84:156–160 (1987). Activity of beta-galactosidase was detected in situ with the substrate 5-bromo-4-chloro-3-indolyl-D-galactosidase, which forms a blue precipitate in infected cells. Price, J. et al., *Proceedings of the National Academy of Sciences, U.S.A.*, 84:156–166 (1987).

Duplicate cultures of infected hepatocytes were analyzed in situ for retrovirus-transduction (and expression) by the cytochemical stain for beta-galactosidase. Price, J. et al., *Proceedings of the National Academy of Sciences, U.S.A.*, 84:156–160 (1987). This procedure specifically labels cells that express viral directed beta-galactosidase; endogenous beta-galactosidase is not detected. FIG. 5 (panels A–D) shows cytochemical localization of beta-galactosidase activity in transduced cultures of hepatocytes and NIH3T3 cells. Panels A–D show hepatocyte cultures plated on type I collagen and infected or days 1, 2, 3, 4, or 5 (panels a–e, respectively). Panel f shows a population of NIH3T3 cells which had been infected with the same viral stocks used to infect hepatocytes on day 3.

Results showed that labeled cells are often found in groups of 2, probably representing infection and integration into a dividing cell with labeling of the two daughter cells. In addition, expression of beta-galactosidase, as determined by the intensity of staining, is quite variable, but tends to be consistent within members of a pair of labeled cells (e.g., see panel C). The efficiency of transduction, as measured cytochemically, exhibited the same dependence on time in culture as was demonstrated by Southern analysis. The fraction of labeled cells increased from less than 1% in cultures infected on day 1 to approximately 25% when infected on day 3; the transduction efficiency dropped dramatically in cultures infected on the next 2 days (days 4 and 5).

Similar analysis of NIH3T3 cells infected with the same viral stock used to infect day 3 hepatocytes indicated that approximately 50% of the cells were labelled. This is consistent with the estimated efficiency of transduction based on Southern blot analysis (FIG. 4, panel A).

Immunocytochemical localization of UDP-glucuronosyltransferase and asialoglycoprotein receptor was performed in the culture dishes using horseradish peroxidase conjugated to protein A (from *Staphylococcus aureus*) and diaminobenzidine cytochemistry at pH 7.4 to detect peroxidase activity. Novikoff, P. M. et al., *Journal of Cell Biology*, 97:1559–1565 (1983). Monospecific IgG to rat UDP-glucuronosyltransferase was purified from rabbit antiserum. Chowdhury et al., used immunocytochemical techniques to determine the distribution of UDP-glucuronosyltransferase in the liver. This membranebound enzyme is present exclusively in hepatocytes and is localized to the endoplasmic reticulum and nuclear membrane. Chowdhury, J. R. et al., *Proceedings of the Nat. Acad. Sci. U.S.A.* 82:2990–2994 (1985). Dr. R. Stockert (Albert Einstein College of Medicine) kindly provided monospecific antibody to rat asialoglycoprotein receptor. Controls for the immunocytochemical experiments included exposure of cells to pre-immune rabbit antisera, followed by identical procedures as those employed for specific rabbit antibody. Immunocytochemical analysis of cultured hepatocytes using the monospecific polyclonal antibody to UDP-glucuronosyltransferase shows reaction product distributed in cytoplasmic clumps and at the periphery of the nucleus in greater than 95% of the cells (FIG. 4, panel G); these reactive sites correspond to the endoplasmic reticulum and the nuclear envelope, respectively. No reaction product is seen in experiments performed with preimmune rabbit IgG (FIG. 5, panel 1).

Asialoglycoprotein receptor

This well described receptor is specifically expressed in hepatocytes. Immunocytochemical analysis in rat liver localizes this receptor to a domain of the plasma membrane which borders the sinusoids; under light microscopy the receptor is seen at the perimeter of the hepatocyte along its sinusoidal face. Genze, J. E. et al., *Journal of Cellular Biology*, 22:867–870 (1982); Matsuura, S. et al., *Journal of Cellular Biology*, 25:864–875 (1982). The level of asialoglycoprotein receptor decreases in culture; however, it is still demonstrated in virtually all cells of a three-day-old hepatocyte culture. Reaction product is seen as a dense line in focal regions of the hepatocyte periphery (FIG. 4, panel H, in which results of localization with a monospecific rabbit antibody are shown). This characteristic staining is absent in experiments with control (preimmune) rabbit serum (FIG. 5, panel 1).

Glucose-6 phosphatase

This glycolytic enzyme is a well recognized cytochemical marker for hepatocytes. It can be detected in virtually all hepatocytes of liver sections. However, there is marked regional variation in enzyme activity; the greatest activity is found in the periportal region. Sasse, D., "Regulation of Hephtic Metabolism and Intra- and Intercellular Compartmentalization, eds. Thurman, R. G., Kauffman, F. C. and Jungermann, K. (Plenum Press, NYC), pp. 57–86 (1986).

Glucose-6-phosphatase activity was detected in three-day-old hepatocyte cultures by the lead phosphate enzyme cytochemical procedure. Wachstein, M. and E. Meisel, *J. Histochem, Cytochem.*, 4:592 (1956).

Characteristic brown/black cytoplasmic staining was seen in greater than 95% of the cells (FIG. 3, panel J). As expected, there was marked cell-to-cell variation in enzyme activity. Activity was not detected in pure cultures of nonparenchymal cells such as fibroblast.

Peroxisomes

The method of Novikoff et al. was used to visualize the distribution of peroxisomes in hepatocyte cultures. Novitoff, A. B. et al., *Histochemistry and Cytochemistry*, 20:1006–1023 (1972). These small cytoplasmic structures (approximately 0.5 microns in diameter) are found specifically in hepatocytes (in the context of the liver) and are visualized by cytochemical staining for catalase. DeDuve, C. et al., *Physiol. Rev.*, 46:323–357 (1966).

Greater than 95% of the cells in the culture tested demonstrated numerous catalase-positive peroxisomes, which appeared as dot-like structures distributed randomly throughout the cytoplasm (FIG. 5, panel K). Peroxisomes were not detected when pure cultures of nonparenchymal cells (e.g., fibroblasts) were analyzed.

EXAMPLE IV

Retrovirus-Mediated Gene Transfer to Correct LDLR Deficiency Isolation, Maintenance and Infection of Hepatocytes Newborn New Zealand white (NZW) rabbits and WHHL rabbits (3–5 days old weighing 50–80 gms) were used as the source of hepatocytes. NZW rabbits have been used as controls in most previous studies of the WHHL rabbit. Newborn WHHL rabbits vere derived from matings between homozygous deficient males and females and were kindly provided by Dr. Knapka (NIH). Four WHHL rabbits from 2 litters (2 rabbits/litter) were used in these studies (named WHHL 1–4). Newborn NZW rabbits were purchased from Pine Acres Rabbitry (West Brattleboro, Vt.). Hepatocytes were prepared using a modification of the procedure of Berry and Friend with the perfusion mixture of Leffert. Berry, M. N. and D. S. Friend, *Journal of Cell Biology*, 43:506–520 (1969). Leffert, H. L. et al., *Methods in Enzymology*, 58:536–544 (1979). Collagenase perfusions were performed retrograde as described by Clayton and Darnell for the preparation of adult mouse hepatocytes. Clayton, D. F. and J. E. Darnell, Jr., *Molecular-Cell Biology*, 3:1552–1561 (1983). Cells were plated at a density of 3–4×10$^4$ cells/cm2 onto Primaria plates (Falcon Co.) in hormonally defined media supplemented with 10% fetal bovine serum; 4–6 hours later the media was replaced with fresh hormonally defined media which was subsequently changed every 24 hours during the duration of the experiment. Enat, R. et al., *Proceedings of the National Academy of Sciences. USA*, 81:1411–1415 (1984).

Hepatocyte cultures were infected for 12 hours with viral stocks (5 ml/10 cm plate) containing Polybrene (8 μg/ml). Unconcentrated viral stocks were prepared from the producer cells as described above.

DNA and RNA Analysis. High-molecular-weight genomic DNA was isolated and analyzed for integration of proviral sequences. Total cellular RNA was prepared using a guanidine thiocyanate procedure, fractionated in formaldehyde/agarose gells and transferred to nitrocellulose paper. Chirgwin, J. M. et al., *Biochemistry*, 18:5294–5299 (1980). Northern and Southern blots were probed with a 1.9 kb LDLR cDNA fragment (Hind III to EcoRI fragment of pTZ1) that was labeled to high specific activity with $^{32}$P-dCTP using the random primer method. Feinberg, A. P. and B. Vogelstein, *Anal. Biochem.*, 132:6–13 (1984). Northern blots were stripped and reprobed with a cDNA probe for human gamma actin (Hind III to Bam HI fragment of pHF-1). Gunning, P. et al., *Molecular Cell Biology*, 3:787–795 (1983).

Cytochemical Analyses. Hepatocytes cultures infected with the BAG virus were analyzed for expression of viral directed beta-galactosidase using a cytochemical stain that forms a blue precipitate in the cytoplasm of transduced cells. Price, J. et al., *Proceedings of the National Academy of Sciences, U.S.A.*, 84:156–160 (1987). Glucose-6-phosphatase activity was detected by the lead phosphate enzyme cytochemical procedure. Wachstein, M. and E. Meisel, *J. Histochem. Cytochem.*, 4:592 (1956). Cultures were analyzed for the presence of LDLR or the receptor for acetylated LDL (AcLDL) by incubating the cultures in hormonally defined media containing fluorescent labeled LDL or AcLDL (labeled with 1,1'-dioctadecyl-3,3,3'3',-tetramethylindocarb acyanine perchlorate—hereafter abbreviated as DiI—at 10 µg/ml, and obtained from Biomedical Tech. Inc., Stoughton, Mass.) for 6–8 hours, followed by three rinses with phosphate buffered saline and fixation in phosphate buffered saline containing 0.5% gluteraldehyde. Pitos, R. E. et al., *Arteriosclerosis*, 1:177–185 (1981). Voyta, J. C. et al., *Journal of Cellular Biology*, 99:81 (1984). Uptake of the fluorescinated reagents was visualized in situ using an inverted Leitz fluorescent microscope.

Assay of LDL Degradation. Five-day-old cultures of hepatocytes plated in 35 mm dishes were assayed for degradation of $^{125}$I-LDL (10 µg/ml, 0.15 µCi/µg, obtained from Biomedical Tech., Inc., Stoughton, Mass.) using the procedure described by Goldstein, Basu and Brown, Goldstein, J. L. et al., *Methods in Enzymology*, 98:241–260 (1983).

Generation of Recombinant Retroviruses Encoding Human LDLR

Four different retroviral vectors were tested; the proviral components of these vectors are presented in FIG. 3. Each vector differs in the transcriptional elements used to drive the expression of LDLR: LTR-LDLR—vital long terminal repeat sequences (LTR); BA-LDLR contains a 267 bp segment of the chicken beta-actin gene (BA) extending from −266 to +1. H4-LDLR contains a 704 bp segment of the histone H4 gene (H4) extending from −696 to +8. TK-LDLR contains a 256 bp segment of the thymidine kinase gene of herpes simplex virus (TK), extending from −200 to +56. Plasmid sequences of LTR-LDLR were derived from the 7.2 Kb Bam HI to Cla I fragment of D01 with the following modification: sequences spanning the Nhe I to Xba I sites of the 3' Moloney murine leukemia virus (NO-MLV) LTR (nuc. 7846 to 8113) were replaced with homologous sequences from the LTR of the myeloproliferative sarcoma virus (represented by darkened area). Korman, A. J. et al., *Proceedings of the National Academy of Sciences, U.S.A.*, 84:2150–2154 (1987); Van Beveren, C. et al., In: *RNA Tumor Viruses* (2nd edition), Weiss, R. et al. (ed.), Cold Spring Harbor Laboratory, pp. 766–783 (19135); Stacey, A. et al., *Journal of Virology*, 50:725–732 (1984).

The backbone structure of plasmids BA-LDLR, H4-LDLR, and TK-LDLR (including the 5'-LTR, flanking mouse genomic DNA, pBR322 sequences, and 3'-LTR with contiguous proviral sequence to the Cla I site at nucleotide 7674) was derived from D01, with the exception that sequences containing the viral enhanced elements of the 3' LTR (from the Pvu II site at nucleotide 7933 to the Xba I site at nucleotide 8111) were deleted (indicated by the inverted triangle). This was done to reduce the amount of viral transcription after reverse transcription and integration of the recombinant provirus. These vectors also contained additional Mo-MLV sequence between the 5' LTR and the internal promoters. The additional sequence was derived from wild type Mo-MLV (from nucleotide 146 at the border of U5 to the Xho I site in the gag coding region-at nucleotide 1560) with the exception that a Sac II linker was inserted at the Hae III site at nucleotide 624. (This additional sequence is noted as gag in the figure). In each case LDLR coding sequences were derived from a 2.6 kb Hind III fragment of plasmid pTZ1 which contains a full-length LDLR cDNA insert (kindly provided by Drs. D. Russell, J. Goldstein and M. Brown). S. D. indicates splice donor site; arrows under each vector show the sites of transcriptional initiation.

Virus producing cell lines for the vector BA-LDLR, H4-LDLR, and TK-LDLR were made by transfecting the particular plasmid DNA with pSV2-Neo into the amphotropic packaging cell line Psi-Crip, as described previously. Cone, R. D. et al., *Molecular and. Cellular Biology*, 7:887–897 (1987); Mulligan, R. C. and P. Berg, *Science*, 209:1422–1427 (1980). Psi-Crip is a modified type of Psi-am packaging cell line which provides cells with the functions of Psi-am (e.g., gag, pol, and env) in two components. That is, the gag-pol function is provided in the form of one integrated provirus and the env function is produced from a separate provirus. The host range is amphotropic.

G418 resistant colonies of cells were expanded and tested for production of virus that transmitted the correct proviral structure. This was done by harvesting supernatants from the producer cells, infecting NIH3T3 cells, and analyzing the infected population for integrated provirus by Southern analysis.

High titer amphotropic producers of the LTR-LDLR vector were obtained using a 2-step procedure. First, high titer ecotropic producers were made by cotransfection of LTR-LDLR with pSV2-Neo into the Psi-2 packaging cell line as described above. Mann, R. et al., *Cell*, 33:153–159 (1983). Psi-Crip cells were then infected with virus harvested from the Psi-2 producer and subsequently split into 10 cm plates at clonal densities. Individual clones were isolated and analyzed for the production of high titer amphotropic virus as described above. Virus-producing cell lines transmitting the highest number of provital copies to recipient cells were chosen for this study. All virus producing cell lines were maintained in culture for 4–6 weeks prior to their use in order to test for the presence of helper virus. None of the cell lines yielded any detectable helper virus nor transferred the packaging functions. An NIH3T3 cell line, designated 7–35, producing amphotropic virus that expresses the gone for human LDL receptor has been deposited (Feb. 3, 1988) under the terms of the Budapest Treaty, with the American Type Culture Collection (Rockville, Md.) under accession number CRL 9635.

Transfer and Expression of LDLR in Hepatocytes

Cells used for the infection studies were hepatocytes isolated from 3 NZW rabbits and 4 WHHL rabbits as described above. Collagenase perfusions routinely produced 40–80×10$^6$ cells/animal with greater than 90% viability. Cells plated at subconfluent densities formed aggregates (5–20 cells/aggregate) that covered approximately 20% of the dish when visualized 6 hours after plating. The primary cultures underwent marked proliferation after 36 hours in culture achieving confluence by day 3 or 4.

To document the cellular composition of the cultures, mock infected WHHL hepatocytes cultured for 5 days were analyzed in several ways. First, the cells were stained for glucose-6-phosphatase, as described above, to determine the number of hepatocytes in the cultures. Glucose-6-phosphatase is a specific marker for hepatocytes in sections of liver and in hepatocyte cultures. More than 95% of the cells had the brown cytoplasmic staining characteristic of hepatocytes. No staining was detectable in pure cultures of fibroblasts or endothelial cells.

In addition, the cultures were analyzed for the presence of endothelial cells and Kupffer cells, since these nonparenchymal cells are abundant in the intact liver and could potentially contaminate the primary cultures. Sinusoidal and capillary endothelial cells as well as Kupffer cells express high levels of the receptor for AcLDL and can be identified in mixed cultures by their selective uptake of Dil-AcLDL. Analysis of the cultured hepatocytes for Dil-AcLDL uptake revealed that approximately 1 in 50 cells were fluorescent. The uptake of Dil-AcLDL by the rare contaminating cells in the hepatocyte cultures was equivalent to that observed in pure secondary cultures of endothelial cells derived from bovine aorta.

To optimize the conditions for infection of the hepatocytes, a high titer amphotropic virus (BAG) encoding E. coli beta-galactosidase was used. Cells transduced by the BAG virus can be detected by a simple cytochemical reaction that stains the cell's cytoplasm blue. Optimal transduction of WHHL hepatocytes was achieved when the cells were plated at subconfluent density and exposed to virus 36 hours after the initial plating. The matrix substrata had little effect on transduction efficiency.

Figure 6:
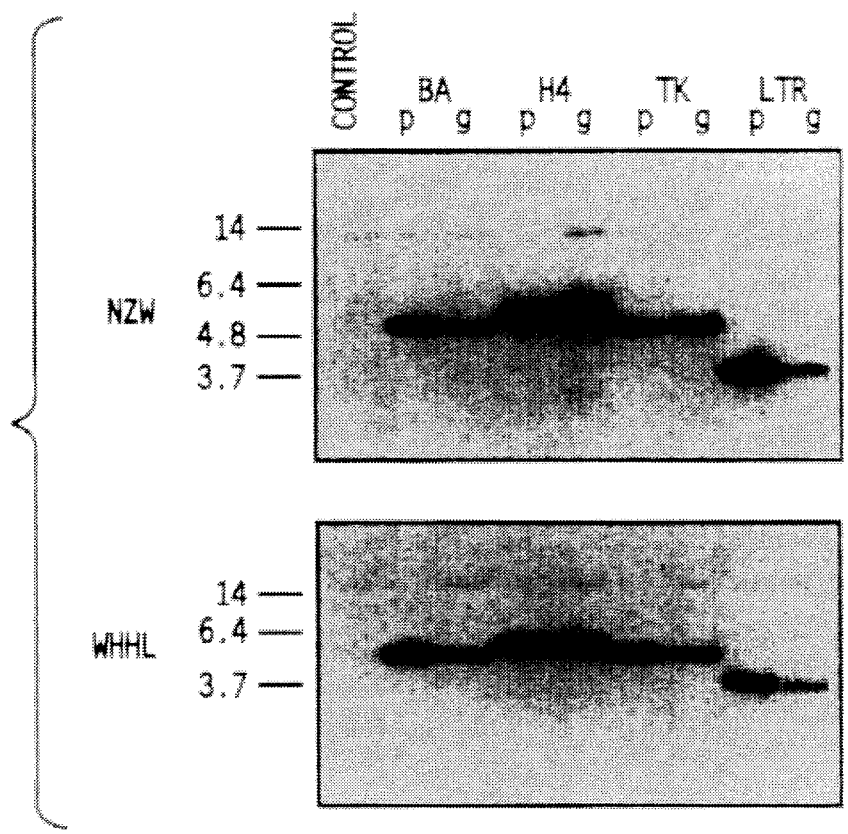
FIG. 6 presents results of a Southern analysis of transduced rabbit hepatocytes.

Having optimized the conditions for infection, NZW and WHHL hepatocytes were infected with the four different LDLR virus preparations 2 days after being placed in culture and vere analyzed for gene transfer and LDLR expression on day 5. Integration of the recombinant provital sequences into the cellular DNA isolated from infected hepatocytes was detected by Southern blot analysis (FIG. 6). DNA from transduced hepatocytes was digested with Kpn I and analyzed by the method of Southern using the LDLR cDNA as a probe. Kpn I has unique recognition sites in the LTR sequences; consequently, each integrated provirus should yield a common restriction fragment irrespective of the site of integration. Each virus producing cell line efficiently transmitted proviral sequences without rearrangement in hepatocytes from both NZW and WHHL rabbits. The relative copy number of integrated provirus varied from a maximum of 1–2 copies/cells for cultures infected with the H4-LDLR virus to a minimum of 0.1 to 0.2 copies/cell for cultures infected with the LTR-LDLR virus. This efficiency of infection was approximately 50% of that achieved in murine fibroblastic cells infected with the same virus preparations.

Additional experiments were performed to show that the viral DNA detected in FIG. 6 was integrated into hepatocyte DNA. DNAs from transduced hepatocytes were digested with Eco RI (a restriction enzyme that has a single site in the proviral DNA) and subjected to Southern analysis using an LDLR probe. If the viral DNA existed as an integrated provirus no distinct Eco RI fragments should be detected because the outer borders of these fragments are located in flanking DNA and therefore are heterogenous. In fact, no Eco RI fragments were detected when this analysis was done, suggesting that the majority of viral DNA was integrated into hepatocyte chromosomal DNA.

Figure 7:
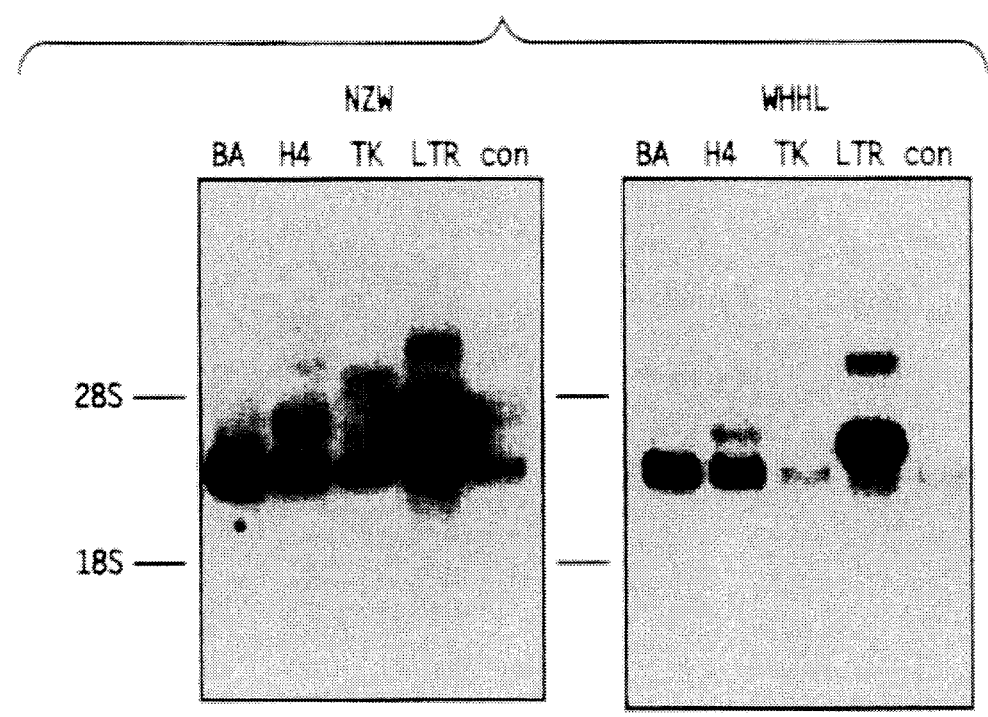
FIG. 7 presents results of a Northern analysis of transduced rabbit hepatocytes.

Transduced cultures-were first analyzed for LDLR expression by Northern analysis (FIG. 7). A faint band with an apparent molecular size equal to 3.5 Kb was detected in mock infected cultures (FIG. 7). This band, which probably represents endogenous LDLR RNA, was consistently more intense in WHHL cultures than in NZW cultures. The predominant RNA species in cultures infected with BA-LDLR, H4-LDLR, and TK-LDLR were the transcripts initiated at the internal promoter. The relative abundance of these RNAs consistently varied in vector-dependent manner as follows: BA-LDLR H4-LDLR TK-LDLR putative endogenous signal. As expected, very little transcription initiated from the LTR of these vectors was detected the enhancer deletion which is present in the 3' LTR of the starting plasmid is transferred to the 5' LTR during proviral passage into hepatocytes. Cultures infected with the LTR-LDLR virus produced a single very intense band representing a transcript initiated at the LTR. All blots were stripped and reprobed with a human gamma-action cDNA probe to control for variation in the amount of RNA that was loaded. There was no detectable variation in the intensity of the gamma-action band suggesting that equal quantities of undegraded RNA were loaded.

Biochemical activity of the exogenous LDLR was assessed in situ by visualizing the uptake of LDL; transduced cultures of hepatocytes were incubated with Dil-LDL and viewed by fluorescent microscopy. Mock infected NZW rabbits exhibited a uniformly high level of fluorescence in all cells; mock infected WHHL hepatocytes showed very little fluorescence. WHHL hepatocytes infected with the LTR-LDLR virus had the greatest amount of LDL uptake with approximately 20% of the cells showing high levels of fluorescence. BA-LDLR infected WHHL hepatocytes demonstrated a population of cells with moderate activity; H4-LDLR infected WHHL hepatocytes showed a low level of activity in virtually all cells. The activity of LDLR in TK-LDLR infected cells was barely over background. The estimate of transduction efficiency based on this in situ assay for LDLR activity agrees with that measured by Southern analysis (e.g., WHHL hepatocytes infected with the LTR-LDLR virus showed fluorescence in approximately 20% of cells while Southern analysis detected a copy number of integrated proviral sequences equal to approximately 0.2).

Transduced hepatocytes were also analyzed for degradation of $^{125}$I-LDL in an attempt to quantify the amount of human LDLR expressed. These data are summarized in the Table. Activity of LDLR was greatest in hepatocytes infected with the LTR-LDLR virus: hepatocytes from a NZW rabbit showed an increase in LDLR activity from 170 ng/mg/5hrs in mock infected cells to 274 ng/mg/5hrs in transduced cells, while cells from WHHL rabbits exhibited an increase in activity from 30–40 ng/mg/5hrs in mock infected cells to 155 (WHHL 1) and 84 (WHHL 3) ng/mg/5 hrs in transduced cells. The level of LDLR activity in LTR-LDLR transduced hepatocytes is approximately 700 ng/mg/5hrs (4 fold greater than the activity of the endogenous receptor in NZW rabbits) when corrected for the actual number of cells that were transduced. Dzierzak, E. A. et al., Nature, 331:35–41 (1987). Hepatocytes infected with viruses that express LDLR from a transcript driven by an internal promoter (i.e., BA-LDLR, H4-LDLR, and TK-LDLR) exhibited little to modest increases in $^{125}$I-LDL degradation.

TABLE 1

Quantitative analysis of $^{125}$I-LDL degradation in transduced hepatocytes[1]

| Virus | $^{125}$I-LDL Degradation (ng/mg protein/5h)[2] | | |
|---|---|---|---|
| | NZW | WHHL-1 | WHHL-3 |
| mock | 170 ± 8[3] | — | 38 ± 5[3] |
| BA-LDLR | 201 ± 10 | — | 42 ± 3 |
| H4-LDLR | 194 ± 9 | 30[4] | 47 ± 3 |
| TK-LDLR | 188 ± 17 | — | 44 ± 8 |
| LTR-LDLR | 274 ± 6 | 155[4] | 84 ± 13 |

[1]Degradation rates were also measured in the presence of 50 fold excess of unlabeled LDL. Under these conditions NZW hepatocytes (mock infected and transduced) had degradation rates that ranged from 50 to 60 ng/mg/5 hrs while WHHL hepatocytes had degradation rates that ranged from 10 to 20 ng/mg/5 hrs.
[2]Analyses were performed on selected cultures of one NZW rabbit and two WHHL rabbits (WHHL 1 and WHHL 3).
[3]Represents mean ±1 S.D. (N-3 for WHHL 3 and N-4 for NZW).
[4]Single determinations.

EXAMPLE V

Introduction of Genetically Modified Hepatocytes into Rabbits

METHODS

Animals. WHHL rabbits used were derived from mating bomozygous LDL receptor deficient rabbits and were obtained from three sources: Dr. Knapka from the National Institutes of Health, Dr. Mahlan from New York University, and from our own breeding colony. Wild type NZW rabbits were purchased from Dutchland Farms (Denver, Pa.). All animals were maintained on a Purina laboratory rabbit chow. Individual animals exhibited less than 2% variation in total serum cholesterol for a period up to 2 weeks prior to hepatocyte transplantation. In addition, baseline pretreatment serum cholesterol levels were indistinguishable between the two major experimental groups: WHHL recipients transplanted with mock infected cells. (539=46 mg/dl, mean±1 S. D., N=6) or LTR-LDLR infected cells (543±48 mg/dl, mean±1 S. D., N=7).

Recombinant Retrovirus. The retroviral vector used to produce amphotropic virus has been described previously, and is depicted in FIG. 9. The vector is derived from a wild type Moloney provirus in which sequences between the Pst I site at n.t. 739 and the Cla I site at n.t. 7674 have been deleted and replaced with Bam HI linkers (for numbering see Van Beveren, C. et al., *RNA Tumor Viruses*, eds. Weiss, R., Teich, N., Varmas, H. & Coffin, J. (Cold Spring Harbor Lab., Cold Spring Harbor, N.Y.), 2nd Ed., pp 766–783 (1985)). Human LDL receptor coding sequences were derived from a 2.6 kb Hind III fragment of plasmid pTZ1 (kindly provided by D. Russell, J. Goldstein, and M. Brown). The Hind III sites were converted to Bcl I sites with synthetic oligonucleotides and the modified fragment was cloned into the BamHI site of the retroviral vector. We mistakenly stated in our initial description of this vector that enhancer sequences in the 3' LTR were replaced with homologous sequences from the myeloproliferative sarcoma virus (Wilson, J. M. et al., *Proc. Natl. Acad. Sci. U.S.A.*, 85:4421–4425 (1988). Subsequent analysis indicated that the 3' LTR of the vector contains Moloney enhancer sequences. The original virus-producing cell line that was generated from this vector was subcloned prior to this study and shown to be free of replication competent virus.

Hepatocyte Isolation and Infection. Rabbit hepatocytes were prepared using the procedure of Berry and Friend, *J. Cell Biol.* 43:506–520 (1969), with a perfusion mixture of Leffert et al., *Methods Enzymol.* 59:536–544 (1979). Cells were plated at a density of 6.7×10$^4$/cm onto a polycation matrix (Primaria, Falcon, Oxnard, Calif.) in a hormonally defined medium supplemented with 10% fetal bovine serum; 4 to 6 hours later the medium was replaced with fresh hormonally defined medium (Enat, R. et al., *Proc. Natl. Acad. Sci. USA* 81:1411–1415 (1984). Two days after the cells were plated, the media were changed to virus-containing media (supplemented with polybrene 8 μg/ml) that was freshly harvested from the virus producing cells (Wilson, J. M. et al., *Proc. Natl. Acad. Sci. USA* 85:4421–4425 (1988)). 12 to 18 hours later, the cells were harvested for transplantation and assayed for gene expression. Cells were detached from the tissue culture plates by incubation in 0.1% trypsin for 10–20 minutes at 37° C. Hepatocytes Transplantation. Animals were prepared for laparotomy and portal vein infusion of hepatocytes with IV pentobaribital anesthesia. Using sterile surgical technique, the abdomen was opened through a 3 cm midline incision, a loop of jejunum externalized, and a tributary of the superior mesenteric vein was identified and secured with ligatures. A prewarmed 8 suspension of hepatocytes (1–2×10$^8$ cells in a volume of 10 ml containing 100 units of heparin) was introduced into the mesenteric vein through a 27 gauge butterfly needle over 5 minutes. The needle was then removed, hemostasis was achieved by tying the ligature, the loop of jejunum returned to the abdomen, and the abdominal incision closed in two layers. The animals received amoxicillin (5 mg/kg body wt, subcutaneously) once daily on the day of surgery and for 5 days after the operation. Venous samples were subsequently obtained through a marginal ear vein and analyzed for total cholesterol as described (Trinder, P., *Annals Clin. Biochem.*, 12: 226–228 (1974)). Selected plasma samples were separated into individual lipoprotein fractions as described (Havel, R. J. et al., *J. Olin. Invest.* 34:1345–1353 (1955)). Molecular Analysis of Gene Transfer and Expression.

Blot Hybridization. High molecular weight DNA was isolated and analyzed by the method of Southern as described (Wilson, J. M. et al., *Proc. Natl. Acad. Sci. USA* 85:4421–4425 (1988)). Total cellular RNA was prepared and analyzed by the method of blot hybridization (Wilson, J. M. et al., *Proc. Natl. Acad. Sci. USA* 85:4421–4425 (1988)). RNA and DNA hybridization filters were probed with $^{32}$P-labeled human LDL receptor cDNA as described (Wilson, J. M. et al., *Proc. Natl, Acad. Sci. USA* 85: 4421–4425 (1988)).

Polymerase Chain Reaction. Proviral sequences were detected in DNA isolated from liver tissue using the polymerase chain reaction (PCR) (Roth, M. S. et al., *Blood* 74:882–885 (1989)). Oligonucleotides used in this reaction have the following sequences:

5'probe-AGGTCAGCTCCACACCCGTAAGGACA-CAGC, and

Figure 9A:
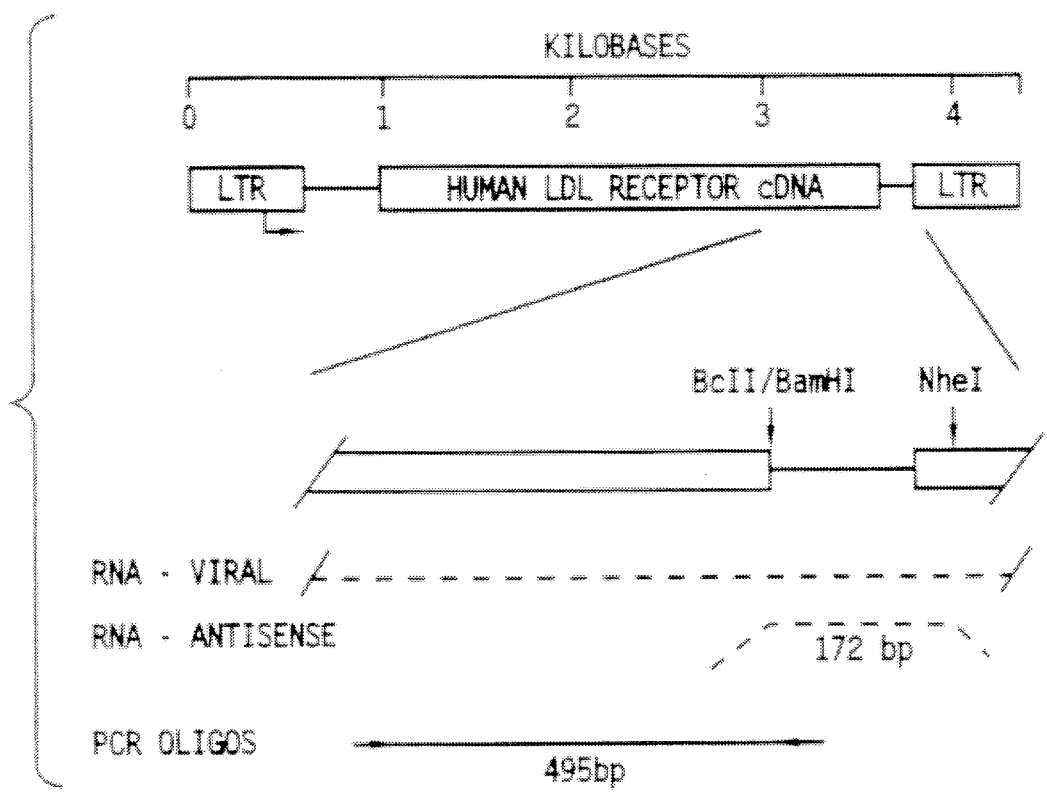
FIG. 9 is a schematic representation of retroviral vector used and shows in vitro characterization of transduced WHHL hepatocytes.
Figure 9B:
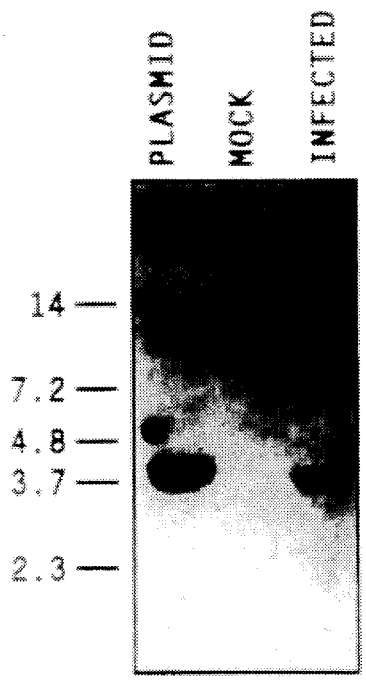
Figure 9C:
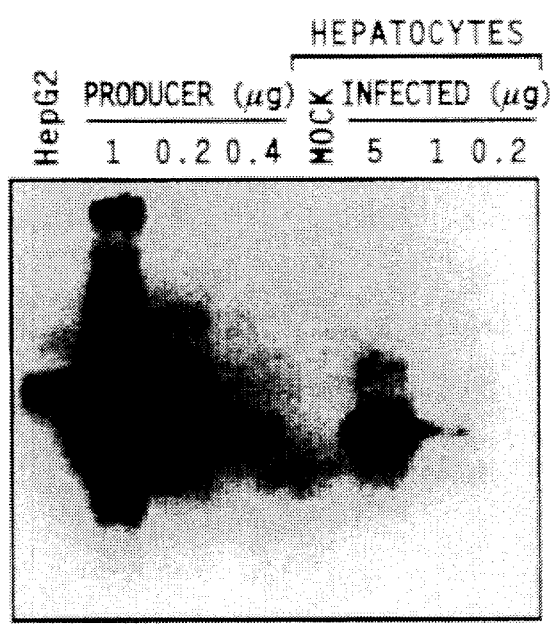

3' probe-GGCTCGTACTCTATAGGCTTCAGCTG-GTGA;

their location within the vector is illustrated in FIG. 9, Panel A.

Ribonuclease Protection Assay. RNA probes were generated from transcription plasmids (Promega Co.) constructed in the following manner. Moloney sequences in the retroviral vector between the synthetic BamHI site at n.t. 7674 and the Nhe I site at n.t. 7846 (1 of 8 for numbering) were cloned between the BamHI and XbaI sites of pGEM-3Z (called 3Z-env); transcription from the SP6 promoter produces antisense RNA that is specific for the virus directed transcript. This BamHI to NheI fragment was also cloned into pGEM-4Z in order to produce sense RNA (4Z-env) from the same promoter. Antisense RNA spanning rabbit LDL receptor coding sequences was used as an internal control in RNase protection experiments. A SmaI to XhoI restriction fragment from a rabbit LDL receptor clone (n.t. 2475 to 2572) (Yamamoto, T. et al., *Science* 232:1230–1237 (1986)) was cloned between the SmaI and SalI sites of pGEM-4Z (4Z-rLDLR). This cDNA was provided by D. Russell. Transcription vectors were linearized by digestion with appropriate restriction endonucleases (3Z-env, EcoRI; 4Z-env, HindIII; and 4Z-rLDLR, HindIII) and used as templates in transcription reactions according to the recommendations of the manufacturer (Promega Co.).

RNase studies were performed on total cellular RNA according to the method of Melton, D. A. et al., *Nucleic Acids Research*, 12:7035–7056 (1986) with several minor modifications. Equal quantities of the viral specific probe and internal control probe were added to each sample. Hybridizations were performed at 55° C. for 12 hours while the RNase A digestion occurred at 37° C. for 1 hour. Radioactivity in the resulting bands were quantified with a Betagen Scanner (Betagen Co.). In Situ Hybridization.

In situ hybridization was performed by a modification of the method described by Pinter and Lugo, in In Situ *Hybridization: Applications to Neurobiology*, eds. Valentino, K. L., Eberwine, J. H. and Barchas, J. D. (Oxford Univ. Press, New York), pp 179–1976. Linearized transcription probes were used as templates in in vitro transcription reactions using SP6 polymerase and UTP($\alpha$) [$^{35}$S]P (Amersham). Radiolabeled RNA probes were isolated and hybridized with cryostat sections at 45° C. for 16 hours in the presence of 50% formamide. The slides were washed at high-stringency conditions, coated with Kodak emulsion NTB-2 and exposed for 4 weeks.

RESULTS

Retrovirus Mediated Gene Transfer into Adult WHHL Hepatocytes. In previous studies, recombinant retroviruses were used to transduce hepatocytes derived from newborn WHHL rabbits with a human LDL receptor gene (Wilson, J. M. et al., *Proc. Natl. Acad. Sci. USA* 85:4421–4425 (1988)). A similar approach was used here to infect hepatocytes derived from adult WHHL animals.

The recombinant virus LTR-LDLR was used in the present studies to infect adult WHHL hepatocytes. The provital form of this virus transcribes a single mRNA that is responsible for expression of LDL receptor and passage of the virus (Wilson, J. M. et al., *Proc. Natl. Acad. Sci. USA* 82:4421–4425 (1988)). WHHL hepatocytes were maintained in hormonally defined medium for 48 hours and subsequently exposed to the LTR-LDLR virus for 12 to 18 hours following the infection, hepatocytes were harvested for transplantation, and analyzed for retrovirus transduction and human LDL receptor expression.

Southern blot analysis of total cellular DNA was used to directly measure the efficiency of gene transfer. These studies demonstrated unrearranged proviral sequences in infected hepatocytes with a relative copy number equal to 0.1 to 0.05 provirus/cell. Duplicate plates of hepatocytes were analyzed for virus directed transcript using RNA transfer blots with a probe that is relatively specific for human LDL receptor RNA. This cDNA probe detected abundant human LDL receptor transcripts in RNA from infected WHHL hepatocytes and a human hepatoblastoma cell line, HepG2. The retrovirus derived transcript is substantially shorter than the endogenous human transcript because the long 3' untranslated region from the endogenous gene was deleted in the retroviral vector. The infection population of hepatocytes had levels of LDL receptor RNA that exceeded endogenous levels in the human hepatoblastoma cell line by 5–6 fold.

Allogeneic Hepatocyte Transplantation.

Techniques for transplanting rabbit hepatocytes were initially developed in an allogeneic system in which hepatocytes were isolated from a strain of rabbits that expresses normal levels of LDL receptor (NZW rabbits) and transplanted into the portal vein of WHHL rabbits. Rabbit recipients were analyzed for changes in total serum cholesterol and, in selected cases, changes in specific lipoprotein fractions. Donor hepatocytes were obtained by in situ collagenase perfusion of adult NZW rabbit livers. Previous experience with this technique in rat animal models suggests that a substantial number of the infused cells seed in the sinusoids of the liver (Patel, A. et al., *Molec. Biol. and Med.* (1989)). Infusion of NZW derived hepatocytes ($1-2 \times 10^8$ cells/animal) into the portal vein of WHHL rabbits led to a reproducible decrease in total serum cholesterol by 25% of pretreatment values (FIG. 10, Panel B). This effect was maximal 3 days after transplantation; serum cholesterol levels subsequently returned to pretreatment levels 10 days after transplantation. Infusion of larger numbers of cells lead to acute portal hypertension as evidenced by blanching of the liver and engorgement of portal vasculature. Nonspecific effects of portal vein directed hepatocyte transplantation on cholesterol metabolism were studied in experiments where donor derived WHHL hepatocytes ($1-2 \times 10^8$ cells/animal) were infused into the portal vein of allogeneic recipient WHHL rabbits (FIG. 9, Panel B). A moderate increase in total cholesterol was actually noted 1 to 2 days following the operation.

Transplantation of Genetically Modified Hepatocytes. Hepatocytes from a single WHHL rabbit were harvested, plated into culture, and mock infected or infected with the LTR-LDLR virus. Following infection, the cells were harvested and transplanted into WHHL recipients via the portal vein ($1-2 \times 10^8$ cells/animal which is approximately 1–4% of the total number of hepatocytes found in the liver). This experiment was repated with three donors and seven recipients (FIG. 10, Panel D). Animals that received LTR-LDLR infected cells demonstrated significant decreases in serum cholesterol on days 2 through 5 following transplantation ($p<0.001$, Student's t test). The peak effect was noted 3 days following transplantation and was associated with a decline in total serum cholesterol to $70\pm3\%$ of pretreatment values (mean±1 S. D., N=7). Transplantation of mock infected WHHL hepatocytes (three donors into six recipients) had no statistically significant effect on serum cholesterol ($p>0.6$, Student's t test) when compared to pretreatment levels (FIG. 10, Panel B). A direct comparison between the control group and the experimental group using the student's test revealed statistically significant decreases in serum cholesterol on days 2 through 6 of the rabbits transplanted with genetically modified hepatocytes ($p<0.001$). Decreases in lipoproteins that are known ligands for LDL receptor (i.e., VLDL, IDL and LDL contribute to the overall diminution in total cholesterol (Table 2)).

TABLE 2

| | Donor | | | | |
|---|---|---|---|---|---|
| Recipient | Hepatocytes | Total | VLDL + IDL | LDL | HDL |
| NZW | Normal control | 40 | 10 | 11 | 19 |
| | | 43 | 11 | 10 | 22 |
| WHHL | NZW | | | | |
| | Pretransplantation: | 650 | 195 | 435 | 20 |
| | 3 days pos-tranplant: | 488 | 169 | 300 | 19 |
| WHHL | NZW | | | | |
| | Pretransplantation: | 620 | 192 | 409 | 19 |
| | 3 days post-transplant: | 446 | 141 | 285 | 20 |
| WHHL | Infected WHHL | | | | |
| | Pretransplantation | 518 | 155 | 315 | 18 |
| | 4 days posttransplantation | 350 | 118 | 212 | 20 |
| WHHL | Infected WHHL | | | | |
| | Pretransplantation | 505 | 150 | 337 | 18 |
| | 4 days posttransplantation | 368 | 130 | 219 | 19 |

Tissues were harvested from transplant recipients in order to perform detailed molecular and cellular analyses of gene transfer and expression. Separate animals were euthanized for tissue harvest at 10 minutes, 24 hours and 19 days following transplantation with genetically modified hepatocytes. Liver tissues were analyzed for proviral DNA sequences using the polymerase chain reaction (FIG. 11) because standard hybridization techniques lacked the necessary sensitivity. Proviral DNA sequences were detected in animals transplanted with infected hepatocytes and sacrificed 10 minutes and 24 hours after transplantation; proviral DNA was no longer detected in liver harvested 19 days after transplantation. Similar analysis of DNA from other tissues, such as lung, failed to detect proviral liver DNA suggesting that most of the hepatocytes seed in sinusoids.

RNase protection analysis was used to detect and quantify the recombinant transcript in total cellular RNA from liver tissue. The recombinant RNA was detected with an antisense probe that is complementary to viral sequences in its 3' untranslated portion (FIG. 9A). Another probe that is specific for endogenous rabbit LDL receptor RNA was incorporated into each assay as an internal control. Analysis of RNA from LTR-LDLR transduced murine fibroblasts demonstrated protection of the 3Z-env probe (172 bp, FIG. 12, Lane A) but not the 4Z-rLDLR probe, while assays of control WHHL RNA revealed no protection of 3Z-env probe with substantial protection of the 4Z-rLDLR probe (98 bp, FIG. 12, Lane C). Each probe produced a band whose intensity varied in proportion to the amount of total cellular RNA used in the initial hybridization. These studies confirm the specificities of the probes and support the use of the assay for quantifying vital and endogenous LDLR receptor transcripts. Virus directed RNA was detected in liver tissue harvested 10 minutes and 24 hours after transplantation with genetically modified hepatocytes (FIG. 12). Quantitative analysis of this experiment indicated that the viral transcript was present at 1–3% of the level of endogenous rLDLR mRNA. No recombinant transcript was detected in liver tissue harvested at 19 days.

Recombinant gene expression was also characterized at the cellular level through the use of in situ hybridization (FIG. 13). The RNA probe complementary to virus specific sequences provided excellent specificity for this in situ detection of human LDL receptor mRNA. In situ hybridization was initially performed with the antisense probe on liver that was harvested 24 hours following transplantation of genetically modified hepatocytes. Approximately 1 in 1000 to 1 in 500 cells contained a high density of cytoplasmic grains (10–100 fold over background).

These positive cells were distributed as single cells in the periportal areas of the liver (FIGS. 13A and B). These hybridization signals were no longer detected in tissues that were analyzed 19 days after transplantation of genetically modified hepatocytes. The specificity of this method is supported by experiments which failed to detect hybridization over background when the antisense probe was hybridized with control WHHL liver, or the sense probe was hybridized with liver from a transplant recipient harvested 24 hours after transplantation.

A variety of highly specific and sensitive molecular techniques were employed to characterize the efficiency of gene transfer and expression in WHHL recipients. One important question relates to the organ and tissue distribution of hepatocyte seeding after infusion of cells into the portal vein. Analysis of tissue DNA for proviral sequences by PCR indicated that most, if not all, of the genetically modified hepatocytes seeded in the liver within 10 minutes of infusion. In situ hybridization of liver tissue revealed virus expressing cells in a periportal distribution. This suggests that the infused hepatocytes lodge in sinusoids soon after leaving the portal venule.

The availability of an authentic animal in combination with sensitive assays for in vivo gene expression provide the opportunity to critically evaluate the efficacy of this proposed therapy. The molecular basis and metabolic consequences of the WHHL mutation have been the subject of extensive investigation (Goldstein, J. L. et al., New Engl. J. Med. 309: 288–296 (1983); Watanabe, Y., Atherosclerosis 36:261–268 (1980); Tanzawa, K. et al, FEPS Letters 118:81–84 (1980); Tanzawa, K. et al., Proc. Natl. Acad. Sci. USA 78:2268–2272 (1981); Bilheimer, D. W. et al., Proc. Natl. Acad. Sci. USA 79:3305–2209 (1982); Kita, T. et al., Proc. Natl. Acad. Sci. USA 79:5693–5697 (1982); Pittman, R. C. et al., J. Biol. Chem. 257:7994–8000 (1982); and Schneider, W. J. et al., Mol Biol. Med. 1:353–367 (1983)). An in-frame deletion in the LDL receptor gene leads to the expression of a dysfunctional receptor molecule that has virtually no detectable activity (Tanzawa, K. et al., FEBS Letters 118:81–84 (1980); Kita, T. et al., Proc. Natl. Acad. Sci. USA 78:2268–2272 (1981); Bilheimer, D. W. et al., Proc. Natl. Acad. Sci. USA 79:3305–2209 (1982); Kita, T. et al., Proc. Natl. Acad. Sci. USA 79:5693–5697 (1982); Pittman, R. C. et al., J. Biol. Chem. 257:7994–8000 (1982); Schneider, W. J. et al., Mol. Biol. Med. 1:353–367 (1983); and Yamamoto, T et al., Science 232:1230–1237 (1986)). Gene replacement was achieved by transplanting a small number of allogeneic WHHL hepatocytes (c.a. 2% of the total hepatocytes in an adult rabbit liver) that express normal levels of human LDL receptor RNA by virtue of retrovirus-mediated gene transfer. Functional replacement of LDL receptor activity should be approximately 2% of normal in transplant recipients. This prediction is in excellent agreement with quantitative analyses of RNA from liver harvested 10 minutes and 24 hours after transplantation which detected the recombinant transcript at 1–3% of the level of the endogenous transcript. This rather modest amount of genetic correction, however, led to a substantial improvement in hypercholesterolemia to 70% of pretreatment levels This finding is consistent with previous studies of homozygous deficient patients in which the level of residual LDL receptor activity was shown to directly correlate with serum cholesterol levels and progression of coronary artery disease (Goldstein, J. L. and M. S. Brown; in *The Metabolic Basis of Inherited Disease*, eds. Scriver, C. R. , Beaudeut, A. L., Sly, W. S. & Valle, D. (McGraw-Hill, Inc.), pp 1215–1250 (1989); Sprecher, D. L. et al., *Metabolism* 94:294–299 (1985)). For example, receptor negative patients (<2% of control receptor activity) have more severe coronary disease and are less responsive to conventional therapies than receptor defective patients (>2% control residual receptor activity). This also suggests that functionally converting a patient from receptor negative to receptor defective status may be metabolically and clinically efficacious.

Metabolic improvements associated with hepatocyte transplantation, however, were not permanent. There are two potential explanations for the apparent deterioration in LDL receptor function in vivo. There could be destruction and actual loss of the genetically modified hepatocytes. Alternatively, the cells may engraft but expression from the recombinant gene may extinguish. In an attempt to differentiate between these possible mechanisms, the integrated provirus was used as a specific and sensitive marker of the genetically modified cells in vivo. Proviral DNA was detected in liver of transplant recipients prior to and during the period of metabolic improvement. The provirus was no longer detected in liver tissue after the total cholesterol returned to baseline. This suggests that cell loss is an important factor in the deterioration of in vivo LDL receptor function. Specific mechanisms responsible for the loss of hepatocyte engraftment remain unclear. We have used similar transplantation methods to demonstrate long term engraftment of hepatocytes in various rat and murine models (Patel, A. et al., *Molec. Biol. and Med.* (1989); Demetriou, A. A. et al., *Science* 233:1190–1192 (1986)). These previous studies, however, used syngeneic or congenic donors, whereas, the present study used allogeneic cells. It is possible that graft rejection due to MHC incompatibility may contribute to the disappearance of genetically modified cells. However, careful histological evaluation of liver tissue failed to reveal foci of inflammation. Alternative explanations include toxicity due to constitutive overexpression of LDL receptor or graft rejection based on an immunological response to the human LDL receptor protein.

In summary, an animal model of familial hypercholesterolemia, the WHHL rabbit, was used to develop a new therapeutic approach in which a normal LDL receptor gene is introduced into genetically deficient hepatocytes which are transplanted into recipient animals at ectopic sites. This intervention resulted in amelioration of the profound hypercholesterolemia that is characteristic of this disorder. More complete and long-term normalization of the hyperlipidemia could potentially be accomplished with greater expression of the transgene in autologous hepatocytes.

EXAMPLE VI

Expression of human parathyroid hormone by rat hepatocytes

Hepatocytes vere isolated from a Wistar rat, as described in Example I. Cells were plated at a density of $10 \times 10^6$ cells onto a bacteriologic plate (10 cm) with 160 mg of cytodex beads and inoculated with hormonally defined medium (HDM) with 10% fetal calf serum. After 90 minutes, the media was replaced with fresh HDM. On day three, the plate was inoculated with viral supernatant from an amphotropic PTH producer (prepared as described in Example II). After 12 hours, the cells were transplanted into an analbuminemic rat (approximately 200 gm intraperitoneally in approximately 5 ml. phosphate buffered saline). Serum was subsequently obtained and analyzed at various times (see FIG. 8) for human PTH, using the commercially-available Nichols radioimmunoassay procedure. Serum was analyzed for rat albumin using Western blot analysis. Results are presented in FIG. 8.

EXAMPLE VII

Construction of the MFG Vector

The MFG vector having the identifying characteristics of ATCC accession No. 68754 is derived from the pEM vector but contains 1038 base pairs of the gag sequence from MMLV to increase the encapsulation of recombinant genomes in the packaging cell lines, and 350 base pairs derived from MOV-9 which contains the splice acceptor sequence and transcriptional start. An 18 base pair oligonucleotide containing NcoI and BamHI sites directly follows the MOV-9 sequence and allows for the convenient insertion of genes with compatible sites. The MMIV LTR controls transcription and the resulting mRNA contains the authentic 5' untranslated region of the native gag transcript followed directly by the open reading frame of the inserted gene. A detailed map of MFG is provided in FIG. 14. Details for the construction of MFG are provided in FIGS. 16(*a*) and 16(*b*).

MFG was constructed by ligating the 5' LTR containing XhoI/NdeI fragment of the half-GAG retroviral vector (half-GAG is described in Bender, et al., *J. Viral.* 6I:1639–1646) to an XhoI/BamHI H4 histone promoter fragment. Retroviral vector pEM was digested with NdeI and BamHI, and the 3' LTR containing fragment was ligated to the half GAG fragment already ligated to the H4 fragment so as to produce an intermediate retrovirus vector containing 2 LTRs in the proper orientation and also containing the H4 fragment within the viral portion of the vector. The intermediate vector was then linearized by digestion with NdeI and the NdeI site in the pB322 portion of the vector was filled in by polymerase and destroyed by ligation. The vector was subsequently digested with XhoI and the XhoI site was joined to an NdeI linker. The vector was subsequently cleaved with BamHI and the large fragment containing both LTRs and the pBR322 sequence) was purified.

A linker having XhoI and BamHI and having the

```
CTAGACTGCCATGGCGCG
    TGACGGTACCGCGCCTAG
``` was synthesized and ligated to both the BamHI site on the cleared intermediate vector and an NdeI/XvaI fragment from pMOV9 [containing a splice acceptor site next to the NdeI edge] so as to form a circular vector, MFG as illustrated in FIG. 14. A plasmid containing vector MFG has been deposited with the American Type Culture Collection and it has accession number 68,754.

The genes for factor VIII and human tPA have been ligated into MFG so as to be operably joined to the viral promotor. These factor VIII and TPA expressing MFG vectors have been deposited with the American Type Culture Collection and given the accession numbers 68726 and 68727 respectively.

EXAMPLE VIII

Construction of α-SGC

The α-SGC vector (ATCC accession number 68755) utilizes transcriptional promoter sequences from the e-globin gene to regulate expression of the tPA gene. The 600 base pair fragment containing the promoter element additionally contains the sequences for the transcriptional initiation and 5' untranslated region of the authentic α-globin mRNA. A 360 base pair fragment which includes the transcriptional enhancer from cytomeglovirus precedes the α-globin promoter and is used to enhance transcription from this element. Additionally, the MMLV enhancer is deleted from the 3' LTR. This deletion is transferred to the 5' LTR upon infection and essentially inactivates the transcriptional activating activity of the element. A detailed description of αSGC is provided in FIG. 15. A plasmid containing the α-SGC vector has been deposited with the American Type Culture Collection and it has accession number 68,755.

The genes for factor VIII and human tPA have been ligated into α-SGC so as to be operably joined to the α globin promoter. These factor VIII and tPA expressing α-SGC vectors have been deposited with the American Type Culture Collection and given the accession numbers 68728 and 68729 respectively.

The following examples provide examples of using the retroviral vectors of the invention using hepatocyte cells.

Biological Deposits

On Oct. 3, 1991, Applicants have deposited with the American Type Culture Collection, Rockville, Md., USA (ATCC) the plasmid MFG with the factor VIII insertion, described herein ATCC accession no. 68726, plasmid MFG with the tPA insertion, described herein, given ATCC accession no. 68727, the plasmid α-SGC, described herein, with the factor VIII insertion, given ATTC ascession no. 68728, and plasmid α-SGC with the tPA insertion, described herein, given ATCC accession no. 68729. On Oct. 9, 1991, Applicants have deposited with the American Type Culture Collection, Rockville, Md., USA (ATCC) the plasmid MFG, described herein, given ATCC accession no. 68754, and plasmid α-SGC, described herein and given ATCC accession no. 68755. An NIH3T3 cell line, designated 7–35, producing amphotropic virus that expresses the gene for human LDL receptor, described herein, having ATCC accession number CRL 9635, has been deposited on Feb. 3, 1988, with the American Type Culture Collection. These deposits were made under the provisions of the Budapest Treaty on the International Recognition of the Deposit of Microorganisms for the purposes of patent procedure and the Regulations thereunder (Budapest Treaty). This assures maintenance of a viable culture for 30 years from date of deposit.

The organisms will be made available by ATCC under the terms of the Budapest Treaty, and subject to an agreement between Applicants End ATCC which assures unrestricted availability upon issuance of the pertinent U.S. patent. Availability of the deposited strains is not to be construed as a license to practice the invention in contravention of the rights granted under the authority of any government in accordance with its patent laws.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. Transduced mammalian hepatocytes having genetic material of interest stably incorporated therein, the transduced hepatocytes being capable of in vivo expression of the polypeptide or protein encoded by the genetic material of interest wherein said genetic material comprises a retroviral vector lacking a selectable marker and selected from the group consisting of α-SGC and MFG.

2. Transduced mammalian hepatocytes of claim 1 in which the genetic material of interest is selected from the group consisting of: DNA which is present in and expressed by normal hepatocytes; DNA which does not normally occurs in hepatocytes but is not expressed in them at levels which are biologically significant; and any DNA which can be modified so that it can be expressed in hepatocytes.

3. Transduced mammalian hepatocytes of claim 2, wherein the genetic material of interest encodes a biologically active protein or polypeptide.

4. Tranduced mammalian hepatocytes of claim 3 wherein the genetic material of interest encodes human parathyroid hormone, tissue plasminogen activator, factor VIII, low density lipoprotein receptor or beta-galactosidase.

5. A method of making transduced mammalian hepatocytes which express stably incorporated genetic material lacking a selectable marker and encoding at least one protein of interest or at,least one polypeptide of interest, comprising the steps of:

a) contacting the hepatocytes in vitro with media containing an infectious recombinant retrovirus having a recombinant genome comprising the "genetic material" for antecedent basis of interest wherein said genetic material comprises a retroviral vector lacking a selectable marker selected from the group consisting of α-SGC and MFG; and b) maintaining the hepatocytes and the media containing the infectious recombinant retrovirus under conditions appropriate for infection of the hepatocytes by recombinant retrovirus, thereby producing transduced hepatocytes.

\* \* \* \* \*

UNITED STATES PATENT AND TRADEMARK OFFICE
CERTIFICATE OF CORRECTION

PATENT NO. : 5,521,076

DATED : May 28, 1996

INVENTOR(S) : Richard C. Mulligan and James M. Wilson

It is certified that errors appear in the above-identified patent and that said Letters Patent is hereby corrected as shown below:

Column 2, line 44, "transcarbalyase" should read --transcarbamlyase--.

Column 3, line 9, "they can be on, (subject to) the retroviral" should read --they can be subject to the retroviral--.

Column 3, line 34, "virus (retroviral) genome." should read --virus genome.--.

Column 4, line 54, "two $^{32}$" should read --two $^{32}$P--.

Column 4, line 57, "virus produced" should read --virus producer--.

Column 4, line 58, "(100ng) plus" should read --(100µg) plus--.

Column 6, line 56, "3' LTRs-serve" should read --3' LTRs serve--.

Column 7, line 9, "R., gill," should read --R., Cell,--.

Column 7, line 46, "which bad be used" should read --which can be used--.

Column 7, line 49, "pVL. The characteristics" should read --pLJ. The characteristics--.

Column 8, line 36, "from. chicken" should read --from chicken--.

Column 8, line 38, "(1986), and thymidine" should read --(1986)), thymidine--.

Column 8, line 40, "*and Cellular* 5" should read --*and Cellular Biology* 5--.

Column 9, line 42, "sequence of interest RNAs" should read --sequence of interest, RNAs--.

Column 9, line 51, "appropriate to-include" should read --appropriate to include--.

Column 9, line 52, "the vector sequences" should read --the vector, sequences--.

UNITED STATES PATENT AND TRADEMARK OFFICE
CERTIFICATE OF CORRECTION

PATENT NO. : 5,521,076

DATED : May 28, 1996

INVENTOR(S) : Richard C. Mulligan and James M. Wilson

It is certified that errors appear in the above-identified patent and that said Letters Patent is hereby corrected as shown below:

Column 4, line 13, "Methods" should read --"Methods".--.

Column 8, line 18, "pip" should read --plp--.

Column 8, line 41, "HindIII/FcoRI" should read --HindIII/EcoRI--.

Column 10, line 51, "hepatocytes vivo." should read --hepatocytes in vivo.--.

Column 13, line 33, "neogene." should read --neo gene.--.

Column 13, line 41, "neogene" should read --neo gene--.

Column 14, line 27, "neogene" should read --neo gene--.

Column 14, line 30, "neogene" should read --neo gene--.

Column 14, line 50, "neogene" should read --neo gene--.

Column 17, line 21, "vital" should read --viral--.

Column 17, line 46, "neogene)." should read --neo gene).--.

Column 20, line 55, "cm2" should read --$cm^2$--.

Column 22, line 50, "provital" should read --proviral--.

Column 22, line 56, "gone" should read --gene--.

Column 23, line 40, "provital" should read --proviral--.

UNITED STATES PATENT AND TRADEMARK OFFICE
CERTIFICATE OF CORRECTION

PATENT NO. : 5,521,076
DATED : May 28, 1996
INVENTOR(S) : Richard C. Mulligan and James M. Wilson It is certified that error appears in the above-indentified patent and that said Letters Patent is hereby corrected as shown below:

Column 11, line 9, "terminal repeats" should read --terminal repeats,--.

Column 11, line 16, "pressure when used when used in vivo" should read --pressure when used in vivo--.

Column 14, line 10, "after introduction-into an" should read --after introduction into an--.

Column 14, line 16, "podified" should read --modified--.

Column 15, line 41, "and animal" should read --an animal--.

Column 17, line 19, "R. gill," should read --R. Cell,--.

Column 17, line 50, "with 32P-dCTP" should read --with $^{32}$P-dCTP--.

Column 18, line 17, "(FIG. 1, panel A)." should read --(FIG. 4, panel A).--.

Column 18, line 60, "A-D" should read --A-F--.

Column 18, line 63, "A-D" should read --A-E--.

Column 18, line 65, "Panel f" should read --Panel F--.

Column 19, line 30, "membranebound" should read --membrane bound--.

Column 19, line 44, "4" should read --5--.

Column 19, line 47, "panel 1" should read --panel I--.

Column 19, line 60, "4" should read --5--.

Column 19, line 64, "panel 1" should read --panel I--.

Column 20, line 4, "Hephtic" should read --Hepatic--.

Column 21, line 3, "gells" should read --gels--.

UNITED STATES PATENT AND TRADEMARK OFFICE
CERTIFICATE OF CORRECTION

PATENT NO. : 5,521,076
DATED : May 28, 1996
INVENTOR(S) : Richard C. Mulligan and James M. Wilson It is certified that error appears in the above-indentified patent and that said Letters Patent is hereby corrected as shown below:

Column 21, line 13, "Hepatocytes" should read --Hepatocyte--.

Column 23, line 39, "vere" should read --were--.

Column 25, line 30, "bomozygous" should read --homozygous--.

Column 27, line 54, "hours following" should read --hours. Following--.

Column 28, line 36, "9" should read --10--.

Column 28, line 46, "repated" should read --repeated--.

Column 28, line 58, "B" should read --C--.

Column 28, line 59, "student's test" should read --Student's t test--.

Column 30, line 42, "animal in" should read --animal model in--.

Column 32, line 1, "vere" should read --were--.

Column 32, line 37, "6l:" should read --61:--.

Column 32, line 60, "[containing" should read --(containing--.

Column 32, line 61, "edge]" should read --edge)--.

UNITED STATES PATENT AND TRADEMARK OFFICE
CERTIFICATE OF CORRECTION

PATENT NO. : 5,521,076
DATED : May 28, 1996
INVENTOR(S) : Richard C. Mulligan and James M. Wilson It is certified that error appears in the above-indentified patent and that said Letters Patent is hereby corrected as shown below:

Column 27, line 48, "provital" should read --proviral--.

Column 29, line 10, "3 days pos-transplant:" should read --3 days post-transplant:--.

Column 29, line 50, "vital" should read --viral--.

Column 32, line 30, "MMIV" should read --MMLV--.

Column 32, line 37, "*J. Viral.*" should read --*J. Virol.*--.

Column 32, line 56, first "T" should line up directly underneath the second "A" in Column 32, line 55.

Column 33, line 10, "e-globin" should read --α-globin--.

Column 34, line 3, "End" should read --and--.

Column 34, lines 26-28, "DNA which does not normally occurs in hepatocytes but is not expressed in them at levels which are biologically significant;" should read --DNA which does not normally occur in hepatocytes; DNA which normally occurs in hepatocytes but is not expressed in them at levels which are biologically significant;--.

Column 34, line 40, "at, least" should read --at least--.

UNITED STATES PATENT AND TRADEMARK OFFICE
CERTIFICATE OF CORRECTION

PATENT NO. : 5,521,076
DATED : May 28, 1996
INVENTOR(S) : Richard C. Mulligan and James M. Wilson It is certified that error appears in the above-indentified patent and that said Letters Patent is hereby corrected as shown below:

Column 34, lines 44-45, ""genetic material" for antecedent basis of" should read --genetic material of--.

Signed and Sealed this

Eleventh Day of August 1998

Attest:

BRUCE LEHMAN

Attesting Officer

Commissioner of Patents and Trademarks